US007265202B1

(12) United States Patent  
Shuai et al.

(10) Patent No.: US 7,265,202 B1  
(45) Date of Patent: Sep. 4, 2007

(54) PIAS MOLECULES THAT RECOGNIZE AND BIND STAT PROTEINS AND USES THEREOF

(75) Inventors: Ke Shuai, Woodland Hills, CA (US); Chan Chung, Los Angeles, CA (US); Jiayu Liao, La Jolla, CA (US); Bin Liu, Los Angeles, CA (US); Xiaoping Rao, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/573,651

(22) PCT Filed: Nov. 27, 1998

(86) PCT No.: PCT/US98/25316

§ 371 (c)(1),  
(2), (4) Date: Nov. 13, 2000

(87) PCT Pub. No.: WO99/28465

PCT Pub. Date: Jun. 10, 1999

Related U.S. Application Data

(60) Provisional application No. 60/069,251, filed on Nov. 28, 1997, provisional application No. 60/095,950, filed on Aug. 10, 1998.

(51) Int. Cl.  
*C07K 1/00* (2006.01)

(52) U.S. Cl. .................. 530/350; 530/300; 530/350; 435/7.1; 435/69.1

(58) Field of Classification Search ............... None  
See application file for complete search history.

(56) References Cited

U.S. PATENT DOCUMENTS 6,518,400 B1 * 2/2003 Karpen et al. ............ 530/350  
6,962,985 B2 * 11/2005 Palm et al. .............. 536/23.1

OTHER PUBLICATIONS

Heinrich et al., Biochemistry Journal, vol. 334, p. 297, 1998.*  
Curr. Opin. Rhematol., 2005, vol. 17, No. 3 p. 305.*  
Liu et al., PNAS, vol. 95, pp. 10626-10631, Sep. 1998.*  
Akira, S. et al., *Cell* 77, 63 (1994). (EXHIBIT 1).  
Chang, D. D., et al., *JCB*, 138,1149 (1997). (EXHIBIT 2).  
Chung, C. D., et al, *Science* 278, 1803 (1997). (EXHIBIT 3).  
Cohen et al., *Proc Acad Sci USA* (1972) 69:2110. (EXHIBIT 4).  
Cohen, G. B., R. Ren, D. Baltimore, *Cell* 80, 237 (1995). (EXHIBIT 5).  
Darnell Jr., et al., *Science* 264, 1415 (1994). (EXHIBIT 6).  
Darnell Jr., J. E., *Science* 277, 1630 (1997). (EXHIBIT 7).  
Durbin, J. E., R. Hackenmiller, M. C. Simon, D. E. Levy, (1996) *Cell* 84:443-450. (EXHIBIT 8).  
Endo, T. A. et al, (1997) Nature 387:921-924. (EXHIBIT 9).

Ferrite, E.J., et al. (Quantitative Comparison of Toxicity of Anti-cancer Agents in Mouse, Rat, Hamster, Dog, Monkey and Man. Cancer Chemother, Rep., 50, No. 4, 219-244, May 1966). (EXHIBIT 10).  
Fu, X. -Y., *Cell* 70, 323 (1992). (EXHIBIT 11).  
Graham et al., *Virol* (1973) 52:456. (EXHIBIT 12).  
Gyuris, J., E. Golemis, H. Chertkov, R. Brent, *Cell* 75, 791 (1993). (EXHIBIT 13).  
Ihle, J. N., *Nature* 377, 591 (1995). (EXHIBIT 14).  
Improta, T., et al, *Proc. Natl. Acad. Sci. USA* 91, 4776 (1994). (EXHIBIT 15).  
Kahn, K. D. et al., *Proc. Natl. Acad. Sci. USA* 90, 6806 (1993). (EXHIBIT 16).  
Meraz, M. A. et al., *Cell* 84, 431 (1996). (EXHIBIT 17).  
Muller, M. et al., *EMBO J.* 12, 4221 (1993). (EXHIBIT 18).  
Naka T. et al., *Nature* 387, 924 (1997). (EXHIBIT 19).  
O'Shea, J. J., *Immunity* 7, 1 (1997). (EXHIBIT 20).  
Pawson, T., J. D. Scott, *Science* 278, 2075 (1997). (EXHIBIT 21).  
Sadowski, H. B., et al., *Science* 261, 1739 (1993). (EXHIBIT 22).  
Schindler, C. and J. E. Darnell Jr., *Annu. Rev. Biochem.* 64, 621 (1995). (EXHIBIT 23).  
Schindler, C., *Proc. Natl. Acad. Sci. USA* 89, 7836 (1992). (EXHIBIT 24).  
Schindler, C., *Science* 257, 809 (1992). (EXHIBIT 25).  
Shuai, K. et al. (1993) Nature 366:580-583. (EXHIBIT 26).  
Shuai, K., et al, *Cell* 76, 821 (1994). (EXHIBIT 27).  
Shuai, K., et al., *Science* 258, 1808 (1992). (EXHIBIT 28).  
Shuai, K., *Science* 261, 1744 (1993). (EXHIBIT 29).  
Southern, *J Mol Biol* (1975) 98:503. (EXHIBIT 30).  
Starr, R. et al., (1997) Nature 387:917-921. (EXHIBIT 31).  
Takeda, K. et al., *Proc. Natl. Acad. Sci. U.S.A.* 94, 3801 (1997).  
Zhong, Z., et al.., *Proc. Natl. Acad. Sci. U.S.A.* 91, 4806 (1995). (EXHIBIT 32).  
Taniguchi, T., *Science* 268, 251 (1995). (EXHIBIT 33).  
Thorpe et al., "The Preparation And Cytotoxic Properties Of Anti-body-Toxin Conjugates", *Immunol. Rev.*, 62:119-58 (1982). (EXHIBIT 34).  
Vaisse, C. et al., *Nature Gen.* 14, 95 (1996). (EXHIBIT 35).  
Valdez, B. C., , *Biochem. Biophys. Res. Commun.* 234, 335 (1997). (EXHIBIT 36).  
Wen, Z., Z. Zhong, J. E. Darnell Jr., *Cell* 82, 241 (1995). (EXHIBIT 37).  
Wigler et al., *Proc Natl Acad Sci USA* (1979) 76:1373-76. (EXHIBIT 38).  
Wu, L., et al, *Mech. of Devel.* 65, 3 (1997). (EXHIBIT 39).  
Zhang, Y. et al., *Nature* 372, 425 (1994). (EXHIBIT 40).  
Zhong, Z., et al., *Science* 264, 95 (1994). (EXHIBIT 41).  
Zhong, Z., et al.., *Proc. Natl. Acad. Sci. U.S.A.* 91, 4806 (1995). (EXHIBIT 42).

* cited by examiner (Continued)

*Primary Examiner*—Hope Robinson  
(74) *Attorney, Agent, or Firm*—Canady & Lortz LLP; Karen S. Canady

(57) ABSTRACT

The invention provides a family of proteins named PIAS which function as specific inhibitors of STAT proteins. Methods of using PIAS molecules are also provided to regulate STAT proteins.

26 Claims, 18 Drawing Sheets

FIG. 1A

```
MVMSFRVSELQVLLGFAGRNKSGRKHELLAKALHLLKSSCAPSVQMKIKELYRRRFPRKTL    61
GPSDLSLLSLPPGTSPPVHPDVTMKPLPFYEVYGELIRPTTLASTSSQRFEEAHFTFALTP   122
QQLQQILTSREVLPGAKCDYTIQVQLRFCLCETSCPQEDYFPPNLFVKVNGKLCPLPGYLP   183
PTKNGAEPRGPAVRSTSHPWLDSQPLSPTPSLLIGHLSLDGITPCPCLVRQLTAGTLLQKL   244
RAKGIRNPDHSRALIKEKLTADPDSEVATTSLPGVTHVPARKMRLTVPCRALTCAHLQSFD   305
AALYLQMNEKKPTWTCPVCDKKAPYESLIIDGLFMEILNSCSDDDEIQFMEDGSWCPMKPK   366
KEASEVCPPPGYGLDGLQYSAVQEGIQPESKKRVEVIDLTIESSSDEEDLPPTKKHCSPTS   427
AAIPALPGSKGALTSGHQPSSVLRSPAMGTLGSDFLSSLPVHEYPPAFPLGADIQGLDLFS   488
FLQTESQQYGPSVIISLDEQDTLGHFFQYRGTPSHFLGPLAPTLGSCHGSSTPAPPPGRVS   549
SIVAPGSSLREGHGGPLPSGPSLTGCRSDVISLD
```

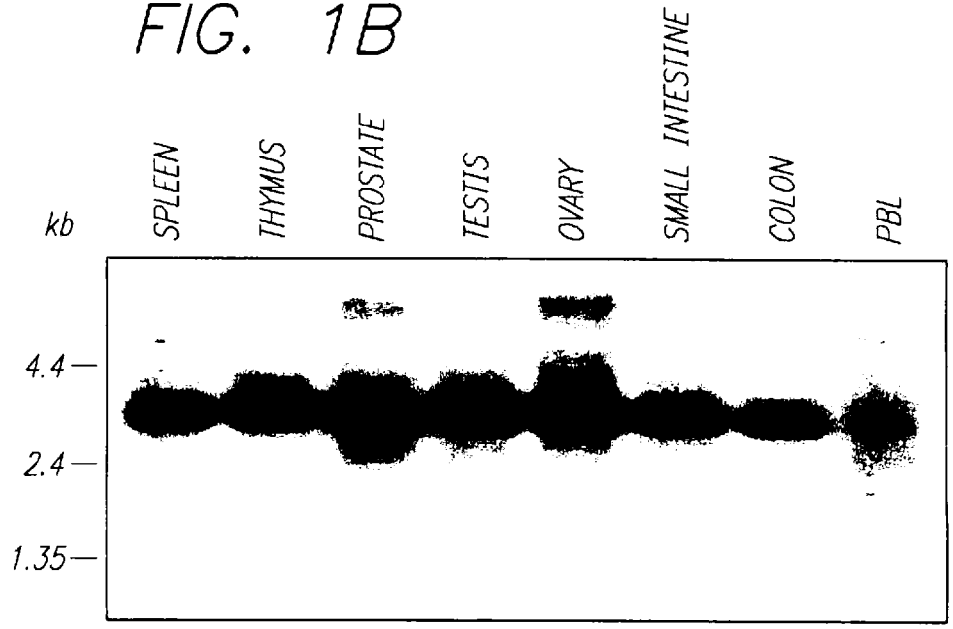

FIG. 1B

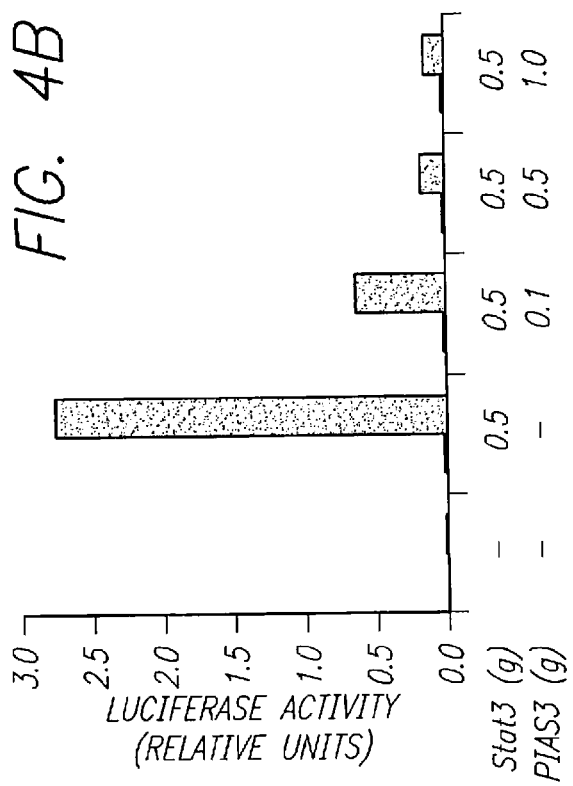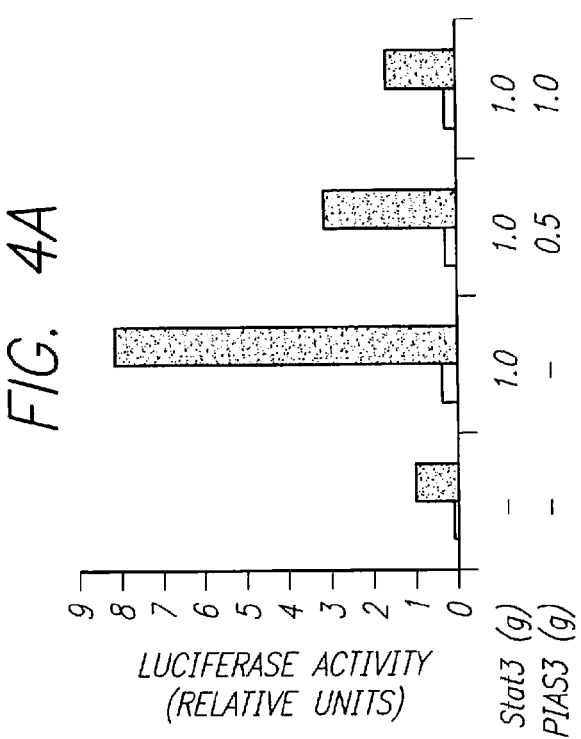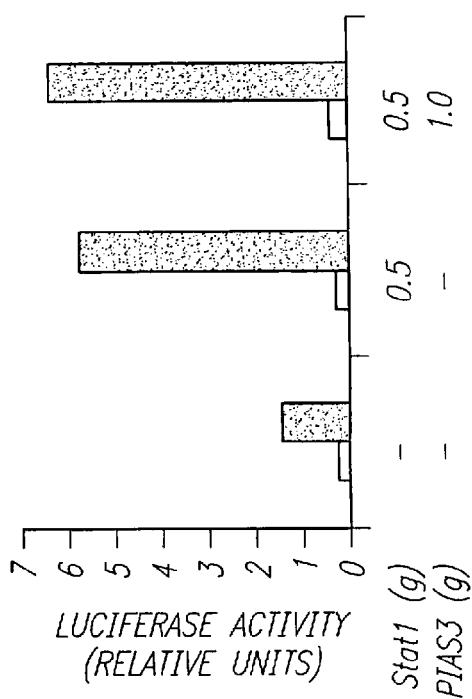
FIG. 4A
FIG. 4B
FIG. 4C

FIG. 5A

```
hPIAS1   MADSAELKQMVMSL RVSELQVLLGYAGRN KHGRKHELLTKALHL LKAGCSPAVQMKIKE LYRRRFPQKIMTPAD LSIPNVH------S    82
mPIAS1   .............. .............. .............. .............. .............. .............S    82
mPIAS3   .....F........ .............. ....S..A...... .SS.A.S....... ........R.TLG.S. .L----LSLPPGT    75
hPIASxα  ...FE.RN..S.F. .............. ....S.....D.MR. ..S......I.R.. ........Y.RTLEGLS. ..TIKSSVFSLDGG.   89
hPIASxβ  ...FE.RN..S.F. .............. ....S.....D.MR. ..S......I.R.. ........Y.RTLEGLS. ..TIKSSVFSLDGG.   89
hPIASy   MA.ELV.A.N....F ...D.M..FV.S .S.L....V.R..Q. VQFD...ELFK.... .............. ------QPHRPL    81 hPIAS1   SPMPATLSPS---TI PQLTYDGHPASSPLL PVSLLGPKHKLELPH LTSALHPVHPDIKLQ KLPFYDLLDELIKPT SLASDNSQRFRETCF   169
mPIAS1   ...P.......... .............. .............. ....E......... .............. ..............   169
mPIAS3   ------------- -------------- -------------- .........VTMK. P......EVYG...R. T....TS....E.AH.   116
hPIASxα  ..VEPD.AVAGIHSL .STSVTP.SP...VG S.L.QDT.PTF.MQQ PSPPIP........ .VQ.K..N....V..V ..VQSSI.....Q.KF.   179
hPIASxβ  ..VEPD.AVAGIHSL .STSVTP.SP...VG S.L.QDT.PTF.MQQ PSPPIP........ .VQ.K..N....V..V ..VQSSI.....Q.KF.   179
hPIASy   D.LTMHSTYDRAGAV .RTPLA.PNIDY.V. YGKY.NGLGR.--- --PAKTLK.EVR.V ...FNM.....L... E.VPQ.NEKLQ.SPC   164
hPIAS1   AFALTPQQVQQISSS MD-ISGTKCDFTVQV QLRFCLSETSCPQED HFPPNLCVKVNTKPC SLPGYLPPTKNGVEP KRPSRPINITSLVRL   258 mPIAS1   .............. .............. .............. .............. .............. ..............   258
mPIAS3   T......L...LT. REVLP.A...Y.I.. ....C......... Y....F....G.L.. P............A. RG.A--VRS..HPW.   204
hPIASxα  I......RE.CI.. R.FLP.GRR.Y... ....L..A...... NY.NS.I...G.LF P......A.P...I.Q ...G..L.......   269
hPIASxβ  I......RE.CI.. R.FLP.GRR.Y... ....L..A...... NY.NS.I...G.LF P......A.P...I.Q ...G..L.......   269
hPIASy   I......R.EL.RKF QGMQP.V.---A... V..I.Y.D...... QY...IA....HSY. V...Y.SN.P.... ....C....L.H.MY.   251 hPIAS1   STTVPNTMC-SWTAE IGR----NYSMAVYL VKQLSSTVLLQRLRA KGIRNPDHSRALIKE KLTADPDSEIATTSL RVSLLCPLGKMRLTI   343
mPIAS1   ...IVV........ .............. .............. .............. ......S....... ..............   344
mPIAS3   DS---QPLSPTPSLL ..HLSLDGITPCPC. .R..TAGT...K... .............. .............. PGVTHV.AR.....V   291
hPIASxα  .SA...QISI.AS.. ..K----....S... VR..T.AM....KM .............. .............. .........M....   355
hPIASxβ  .SA...QISI.AS.. ..K----....S... VR..T.AM....KM .............. .............. .........M....   355
hPIASy   .SAT-.RITVT.GNY -.K.....S.V.L.. VR..T.SE.....KT I.VKH.ELCK..V.. ......RL...... ......GV...I..V....SV   335
```

```
1/1                             31/11
atg gtg atg agt ttc cgg gtg tct gag ctc cag gtg ctt ctt ggc ttt gct ggc cgg aac
 M   V   M   S   F   R   V   S   E   L   Q   V   L   L   G   F   A   G   R   N
61/21                           91/31
aag agt gga cgg aag cac gag ctc ctg gcc aag gct ctg cac ctc ctg aag tcc agc tgt
 K   S   G   R   K   H   E   L   L   A   K   A   L   H   L   L   K   S   S   C
121/141                         151/51
gcc cct agt gtc cag atg aag atc aaa gag ctt tac cga cga cgc ttt ccc cgg aag acc
 A   P   S   V   Q   M   K   I   K   E   L   Y   R   R   R   F   P   R   K   T
181/61                          211/71
ctg ggg ccc tct gat ctc tcc ctt ctc tct ttg ccc cct ggc acc tct cct cct gtg cac
 L   G   P   S   D   L   S   L   L   S   L   P   P   G   T   S   P   P   V   H
241/81                          271/91
cct gat gtc acc atg aaa cca ttg ccc ttc tat gaa gtc tat ggg gag ctc atc cgg ccc
 P   D   V   T   M   K   P   L   P   F   Y   E   V   Y   G   E   L   I   R   P
301/101                         331/111
acc acc ctt gca tcc act tct agc cag cgg ttt GAG GAA GCG CAC TTT ACC TTT GCC CTC
 T   T   L   A   S   T   S   S   Q   R   F   E   E   A   H   F   T   F   A   L
361/121                         391/131
ACA CCC CAG CAA GTG CAG CAG ATT CTT ACA TCC AGA GAG GTT CTG CCA GGA GCC AAA TGT
 T   P   Q   Q   V   Q   Q   I   L   T   S   R   E   V   L   P   G   A   K   C
421/141                         451/151
GAT TAT ACC ATA CAG GTG CAG CTA AGG TTC TGT CTC TGT GAG ACC AGC TGC CCC CAG GAA
 D   Y   T   I   Q   V   Q   L   R   F   C   L   C   E   T   S   C   P   Q   E
481/161                         511/171
GAT TAT TTT CCC CCC AAC CTC TTT GTC AAG GTC AAT GGG AAA CTG TGC CCC CTG CCG GGT
 D   Y   F   P   P   N   L   F   V   K   V   N   G   K   L   C   P   L   P   G
541/181                         571/191
TAC CTT CCC CCA ACC AAG AAT GGG GCC GAG CCA AGA GGC CCA GCC GCC CCA TCA ACA TCA
 Y   L   P   P   T   K   N   G   A   E   P   R   G   P   A   A   P   S   T   S
601/201                         631/211
CAC CCC TGG CTC GAC TCT CAG CCA CTG TTC CCA ACA CCA TTG TGG TCA ATT GGT CAT CTG
 H   P   W   L   D   S   Q   P   L   F   P   T   P   L   W   S   I   G   H   L
661/221                         691/231
AGT TCG GAC GGA ATT ACT CCT TGT CTG TGT ACC TtG GTG AGG CAG TTG ACT GCA GGA ACC
 S   S   D   G   I   T   P   C   L   C   T   L   V   R   Q   L   T   A   G   T
721/241                         751/251
CTT CTA CAA aaa ctc aga gca aag ggt atc cgg aac cca gac cac tcg cgg gca ctg atc
 L   L   Q   K   L   R   A   K   G   I   R   N   P   D   H   S   R   A   L   I
781/261                         811/271
aag gag aaa ttg act gct gac cct gac agt gag gtg gcc act aca agt ctt ccg ggt gtc
 K   E   K   L   T   A   D   P   D   S   E   V   A   T   T   S   L   P   G   V
841/281                         871/291
act cat gtg ccc gct agG aag atg cgc ctg act gtc cct tgt cgt gcc ctc acc tgc gcc
```

```
                              T   H   V   P   A   R   K   M   R   L       T   V   P   C   R   A   L   T   C   A
901/301                                                       931/311
cac ctg cag agc ttc gat gct gcc ctt tat   cta cag atg aat gag aag aag cct aca tgg
961/321                                                       991/331
aca tgt cct gtg tgt gac aag aag gct ccc   tat gaa tct ctt atc att gat ggt tta ttt
 T   C   P   V   C   D   K   K   A   P     Y   E   S   L   I   I   D   G   L   F
1021/341                                                      1051/351
atg gag att ctt agt tcc tgt tca gat tgt   gat gag atc caa ttc atg gaa gat gga tcc
 M   E   I   L   S   S   C   S   D   C     D   E   I   Q   F   M   E   D   G   S
1081/361                                                      1111/371
tgg tgc cca atg aaa ccc aag aag gag gca   tct gag gtt tgc ccc ccg cca ggg tat ggg
 W   C   P   M   K   P   K   K   E   A     S   E   V   C   P   P   P   G   Y   G
1141/381                                                      1171/391
ctg gat ggc ctc cag tac agc cca ggt cca   ggg ggg aga tcc atc gag aat aag aag aag
 L   D   G   L   Q   Y   S   P   G   P     G   G   R   S   I   E   N   K   K   K
1201/401                                                      1231/411
gtc gaa gtt att gac ttg aca ata gaa agc   tca tca gat gag gag gat ctg ccc cct acc
 V   E   V   I   D   L   T   I   E   S     S   S   D   E   E   D   L   P   P   T
1261/421                                                      1291/431
aag aag cac tgt tct gtc acc tca gct gcc   atc ccg gcc cta cct gga agc aaa gga gtc
 K   K   H   C   S   V   T   S   A   A     I   P   A   L   P   G   S   K   G   V
1321/441                                                      1351/451
ctg aca tct ggc cac cag cca tcc tcg gtg   cta agg agc cct gct atg ggc acg ttg ggt
 L   T   S   G   H   Q   P   S   S   V     L   R   S   P   A   M   G   T   L   G
1381/461                                                      1411/471
ggg gat ttc ctg tcc agt ctc cca cta cat   gag tac cca cct gcc ttc cca ctg gga gcc
 G   D   F   L   S   S   L   P   L   H     E   Y   P   P   A   F   P   L   G   A
1441/481                                                      1471/491
gac atc caa ggt tta gat tta ttt tca ttt   ctt CAG ACA GAG AGT cag cac tat ggc ccc
 D   I   Q   G   L   D   L   F   S   F     L   Q   T   E   S   Q   H   Y   G   P
1501/501                                                      1531/511
tct gtc atc atc tca cta gat gaa cag gat   gcc ctt ggc cac ttc tTc cag tac cga ggg
 S   V   I   I   S   L   D   E   Q   D     A   L   G   H   F   F   Q   Y   R   G
1561/521                                                      1591/531
acc cct tct cac ttt ctg ggc cca ctg gcc   ccc acg ctg ggg agc tcc cac tgC agc gcc
 T   P   S   H   F   L   G   P   L   A     P   T   L   G   S   S   H   C   S   A
1621/541                                                      1651/551
act ccg gcg ccc cct cct ggC cgt gtc agc   agc att gtg gcc cct ggg ggg gcc ttg agg
 T   P   A   P   P   P   G   R   V   S     S   I   V   A   P   G   G   A   L   R
1681/561                                                      1711/571
gag ggg cat gga gga ccc ctg ccc tca ggt   ccc tct Ttg act ggc tgt cgg tca gac atc
 E   G   H   G   G   P   L   P   S   G     P   S   L   T   G   C   R   S   D   I
1741/581
att tcc ctg gac tga
 I   S   L   D   *
```

FIG. 5B-2

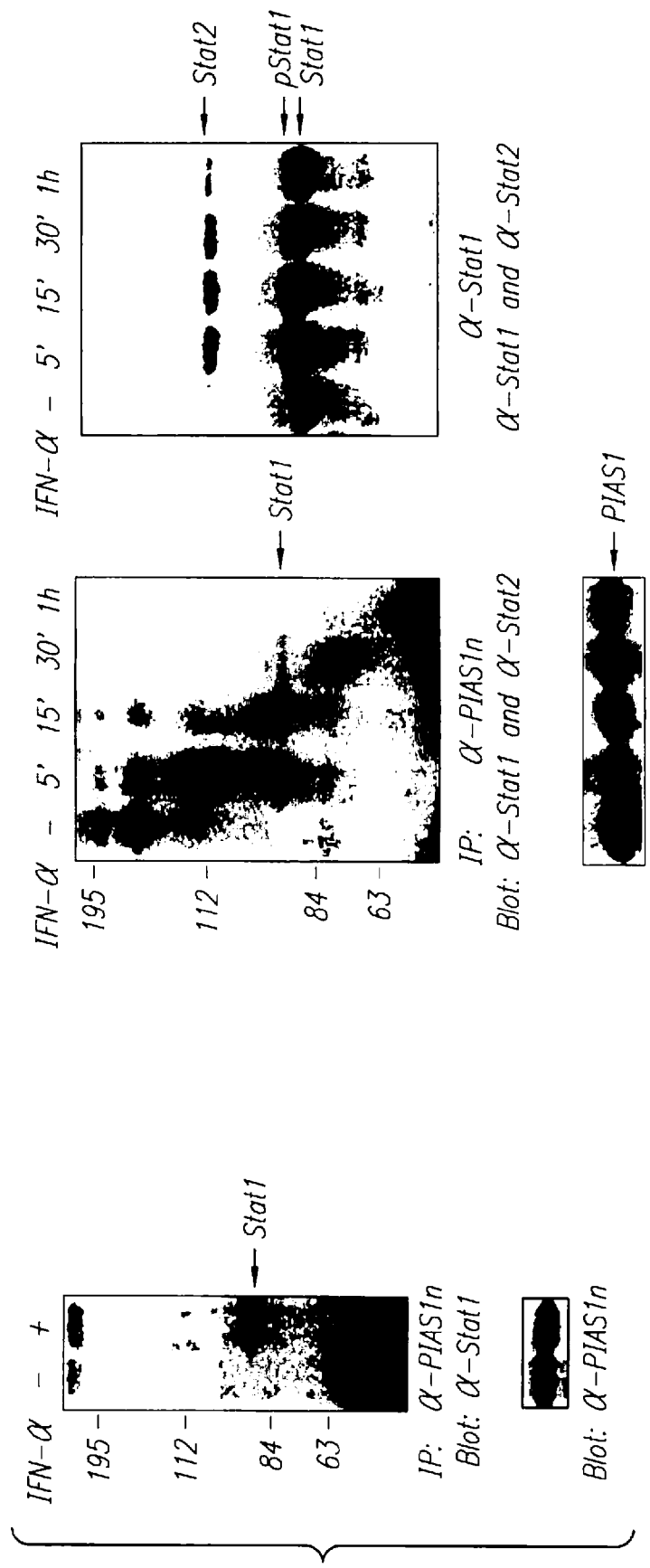
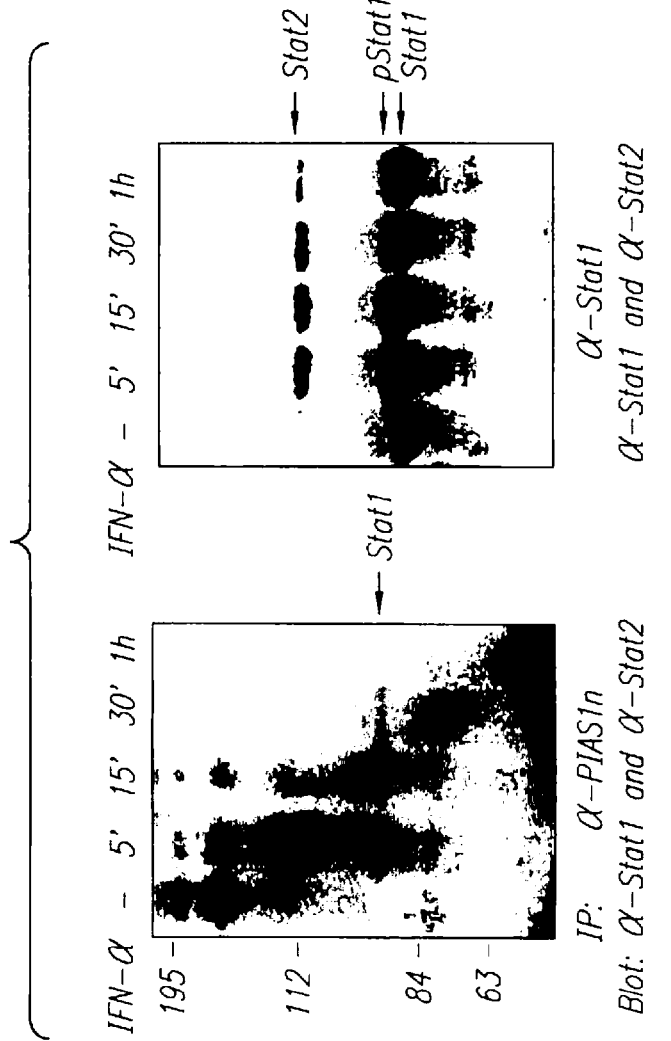
FIG. 8B
FIG. 8A

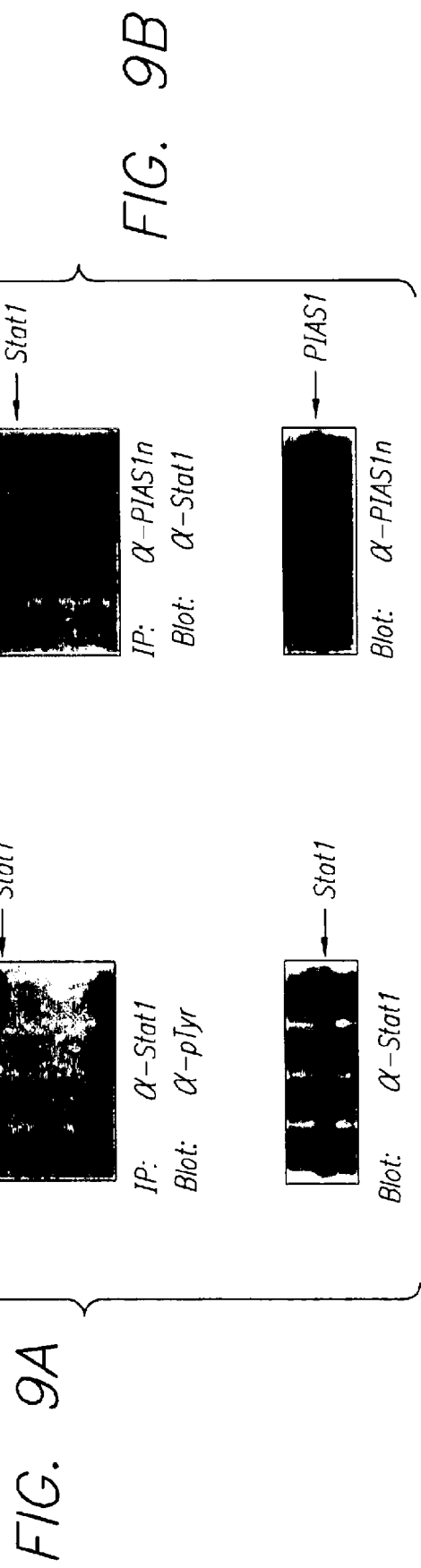

FIG. 10-1

```
1/1                                     31/11
ATG GCG GAC AGT GCG GAA CTA AAG CAA ATG GTT ATG AGC CTT AGA GTT TCT GAA CTC CAA
 M   A   D   S   A   E   L   K   Q   M   V   M   S   L   R   V   S   E   L   Q
61/21                                   91/31
GTA CTG TTG GGC TAC GCT GGG AGG AAC AAG CAC GGA CGC AAA CAC GAA CTT CTT ACA AAA
 V   L   L   G   Y   A   G   R   N   K   H   G   R   K   H   E   L   L   T   K
121/41                                  151/51
GCC CTG CAT TTG TTA AAG GCT GGC TGT AGT CCT GCT GTA CAA ATG AAA ATT AAA GAA CTC
 A   L   H   L   L   K   A   G   C   S   P   A   V   Q   M   K   I   K   E   L
181/61                                  211/71
TAC AGG AGG CGG TTC CCT CAG AAA ATT ATG ACG CCT GCG GAC TTG TCT ATC CCC AAC GTA
 Y   R   R   R   F   P   Q   K   I   M   T   P   A   D   L   S   I   P   N   V
241/81                                  271/91
CAT TCA AGT CCT ATG CCT CCG ACT CTT TCT CGA TCC ACC ATT CCA CAG CTC ACT TAT GAT
 H   S   S   P   M   P   P   T   L   S   P   S   T   I   P   Q   L   T   Y   D
301/101                                 331/111
GGC CAC CCT GCA TCA TCC CCA CTA CTC CCT GTT TCT CTT CTG GGA CCC AAA CAT GAA CTG
 G   H   P   A   S   S   P   L   L   P   V   S   L   L   G   P   K   H   E   L
361/121                                 391/131
GAA CTC CCA CAT CTC ACG TCA GCG CTG CAC CCA GTC CAC CCQ GAC ATA AAG CTG CAG AAG
 E   L   P   H   L   T   S   A   L   H   P   V   H   P   D   I   K   L   Q   K
421/141                                 451/151
CTA CCA TTC TAT GAC CTG TTG GAT GAA CTG ATC AAG CCC ACC AGT CTA GCT TCA GAC AAC
 L   P   F   Y   D   L   L   D   E   L   I   K   P   T   S   L   A   S   D   N
481/161                                 511/171
AGC CAG CGC TTT CGG GAA ACC TGT TTT GCA TTT GCC TTG ACA CCA CAA CAG GTG CAG CAG
 S   Q   R   F   R   E   T   C   F   A   F   A   L   T   P   Q   Q   V   Q   Q
541/181                                 571/191
ATC AGC AGC TCC ATG GAT ATT TCT GGG ACC AAA TGT GAC TTC ACA GTG CAG GTC AAA TTA
 I   S   S   S   M   D   I   S   G   T   K   C   D   F   T   V   Q   V   Q   L
601/201                                 631/211
AGG TTT TGT TTA TCA GAA ACC AGT TGT CCA CAA GAA GAT CAC TTC CCA CCC AAC CTT TGT
 R   F   C   L   S   E   T   S   C   P   Q   E   D   H   F   P   P   N   L   C
661/221                                 691/231
GTA AAA GTG AAT ACA AAA CCT TGC AGC CTT CCA GGT TAC CTT CCA CCT ACT AAA AAC GGT
 V   K   V   N   T   K   P   C   S   L   P   G   Y   L   P   P   T   K   N   G
721/241                                 751/251
GTG GAA CCA AAG CGA CCT AGC CGA CCA ATT AAT ATC ACC TCA CTT GTC CGA TTG TCC ACG
 V   E   P   K   R   P   S   R   P   I   N   I   T   S   L   V   R   L   S   T
781/261                                 811/271
ACA GTA CCA AAT ACC ATT GTT GTT TCT TGG ACT GCA GAA ATT GGA AGA ACC TAT TCC ATG
 T   V   P   N   T   I   V   V   S   W   T   A   E   I   G   R   T   Y   S   M
841/281                                 871/291
GCA GTA TAT CTT GTA AAA CAG TTG TCC TCA ACA GTT CTT CTT CAG AGG TTA CGA GCA AAG
```

FIG. 10-2

```
A   V   Y   L   V   K   Q   L   S   S   T   V   L   L   Q   R   L   R   A   K
901/301                                 931/311
GGA ATA AGG AAT CCG GAT CAT TCT AGA GCT TTA ATT AAA GAG AAG TTA ACT GCA GAT TCA
G   I   R   N   P   D   H   S   R   A   L   I   K   E   K   L   T   A   D   S
961/321                                 991/331
GAT AGT GAG ATA GCT ACT ACC AGC CTA CGG GTT TCG CTG CTG TGT CCA CTT GGG AAA ATG
D   S   E   I   A   T   T   S   L   R   V   S   L   L   C   P   L   G   K   M
1021/341                                1051/351
CGA CTG ACA ATC CCC TGT CGG GCA CTT ACC TGC TCC Cac ctt cag tgt ttt gat gca act
R   L   T   I   P   C   R   A   L   T   C   S   H   L   Q   C   F   D   A   T
1081/361                                1111/371   ↓
ctt tac att caa atg aat gag aaa aaa cca aca tgg gtt tgt cct gtc tgt gat aag aag
L   Y   I   Q   M   N   E   K   K   P   T   W   V   C   P   V   C   D   K   K
1141/381                                1171/391
gcc cca tat gaa cac ctt att att gac ggg ttg ttt atg gaa att cta aag tac tgc aca
A   P   Y   E   H   L   I   I   D   G   L   F   M   E   I   L   K   Y   C   T
1201/401                                1231/411
gac tgt gac gag ata cag ttt aag gag gat ggc tcg tgg gct cca atg agg tca aag aag
D   C   D   E   I   Q   F   K   E   D   G   S   W   A   P   M   R   S   K   K
1261/421                                1291/431
gag gtt caa gaa gtc act gcc tcc tac aat gga gtt gat ggt tgc ttg agc tcc aca ttg
E   V   Q   E   V   T   A   S   Y   N   G   V   D   G   C   L   S   S   T   L
1321/441                                1351/451
gag cat cag gta gcg tcc cac aac cag tcc tca aat aaa aac aag aaa gtc gag gtc att
E   H   Q   V   A   S   H   N   Q   S   S   N   K   N   K   K   V   E   V   I
1381/461                                1411/471
gac cta acc att gac agc tcg tca gat gaa gag gag gaa gAA CCC CCT GCC AAG AGG ACC
D   L   T   I   D   S   S   S   D   E   E   E   E   P   P   A   K   R   T
1441/481                                1471/491
TGT CCT TCC CTG TCT CCT ACG TCA CCA CTA AGT AAT AAA GGC ATT TTA AGT CTT CCT CAT
C   P   S   L   S   P   T   S   P   L   S   N   K   G   I   L   S   L   P   H
1501/501                                1531/511
CAA GCC TCG CCT GTG TCC CGC ACC CCA AGC CTT CCT GCT GTA GAT ACA AGC TAC ATC AAC
Q   A   S   P   V   S   R   T   P   S   L   P   A   V   D   T   S   Y   I   N
1561/521                                1591/531
ACC TCC CTC ATC CAG GAC TAC AGG CAC CCC TTC CAC ATG ACG CCT ATG CCT TAT GAC TTA
T   S   L   I   Q   D   Y   R   H   P   F   H   M   T   P   M   P   Y   D   L
```

FIG. 10-3

```
1621/541                           1651/551
CAA GGA TTA GAT TTC TTT CCT TTC TTA TCA GGA GAC AAT CAG CAT TAC AAC ACC TCC CTG
 Q   G   L   D   F   F   P   F   L   S   G   D   N   Q   H   Y   N   T   S   L
1681/561                           1711/571
CTA GCC GCA GCT GCA GCG GCG GTC TCA GAT GAC CAG GAC CTC CTG CAC TCC TCC CGG TTT
 L   A   A   A   A   A   A   V   S   D   D   Q   D   L   L   H   S   S   R   F
1741/581                           1771/591
TTC CCG TAT ACC TCC TCG CAG ATG TTT CTC GAC CAG CTA AGT GCA GGA GGG AGC ACA TCT
 F   P   Y   T   S   S   Q   M   F   L   D   Q   L   S   A   G   G   S   T   S
1801/601                           1831/611
CTG CCA GCC ACC AAC GGA AGC AGT AGC GGC AGC AAC AGC AGC CTT GTG TCT TCC AAC AGT
 L   P   A   T   N   G   S   S   S   G   S   N   S   S   L   V   S   S   N   S
1861/621                           1891/631
CTG AGA GAG AGC CAT GGC CAT GGT GTG GCC AGC AGG AGC AGC GCA GAC ACA GCG TCC ATC
 L   R   E   S   H   G   H   G   V   A   S   R   S   S   A   D   T   A   S   I
1921/641                           1951/651
TTT GGC ATC ATA CCA GAC ATT ATC TCA TTG GAC TGA
 F   G   I   I   P   D   I   I   S   L   D   *
```

FIG. 11-1

```
1/11                                    31/11
ATG GTG ATG AGT TTC CGA GTG TCT GAG CTC CAG GTG CTC CTC GGC TTC GCT GGC AGG AAC
 M   V   M   S   F   R   V   S   E   L   Q   V   L   L   G   F   A   G   R   N
61/21                                   91/31
AAG AGT GGG CGG AAA CAC GAG CTG CTG GCC AAG GCC CTG CAC CTC CTC AAG TCT AGC TGC
 K   S   G   R   K   H   E   L   L   A   K   A   L   H   L   L   K   S   S   C
121/41                                  151/51
GCC CCC AGC GTC CAG ATG AAG ATC AAA GAA CTT TAT CGC AGG CGC TTT CCC CGG AAG ACC
 A   P   S   V   Q   M   K   I   K   E   L   Y   R   R   R   F   P   R   K   T
181/61                                  211/71
CTG GGG CCT TCT GAT CTC TCC TTG CTT TCT TTG CCC CCT GGC ACC TCT CCT CCT GTG CAC
 L   G   P   S   D   L   S   L   L   S   L   P   P   G   T   S   P   P   V   H
241/81                                  271/91
CCC GAT GTC ACC ATG AAG CCA CTG CCC TTC TAT GAA GTC TAT GGG GAG CTC ATC CGA CCC
 P   D   V   T   M   K   P   L   P   F   Y   E   V   Y   G   E   L   I   R   P
301/101                                 331/111
ACC ACC CTT GCG TCC ACC TCC AGC CAG AGG TTC GAG GAA GCC CAC TTC ACC TTC GCG CTC
 T   T   L   A   S   T   S   S   Q   R   F   E   E   A   H   F   T   F   A   L
361/121                                 391/131
ACT CCC CAG CAG CTG CAG CAG ATT CTC ACG TCC AGG GAA GTT CTG CCA GGA gCC AAG TGT
 T   P   Q   Q   L   Q   Q   I   L   T   S   R   E   V   L   P   G   A   K   C
421/141                                 451/151
GAT TAC ACC ATA CAA GTG CAG CTC AGA TTC TGT CTC TGT GAG ACC AGC TGC CCT CAG GAG
 D   Y   T   I   Q   V   Q   L   R   F   C   L   C   E   T   S   C   P   Q   E
481/161                                 511/171
GAC TAT TTC CCC CCT AAC CTC TTT GTT AAG GTT AAT GGG AAA CTC TGC CCC CTG CCG GGT
 D   Y   F   P   P   N   L   F   V   K   V   N   G   K   L   C   P   L   P   G
541/181                                 571/191
TAC CTC CCT CCA ACC AAG AAT GGA GCT GAG CCC AGA gGC CCA GCC GTC CGA TCA ACA TCA
 Y   L   P   P   T   K   N   G   A   E   P   R   G   P   A   V   R   S   T   S
601/201                                 631/211
CAC CCT TGG CTC GAC TCT CAG CCA CTG TCC CCA ACA CCA TCG Tta TTA ATT GGT CAT CTG
 H   P   W   L   D   S   Q   P   L   S   P   T   P   S   L   L   I   G   H   L
561/221                                 691/231
AGT TTG GAC GGA ATT ACT CCT TGT CCG TGT CTG GTG AGG CAA TTG ACT GCA GGG ACC CTT
 S   L   D   G   I   T   P   C   P   C   L   V   R   Q   L   T   A   G   T   L
721/241                                 751/251
CTA CAA AAA CTC AGA GCC AAG GGG ATC CGG AAT CCA GAC CAT TCC CGG GCA CTG ATC AAG
 L   Q   K   L   R   A   K   G   I   R   N   P   D   H   S   R   A   L   I   K
781/261                                 811/271
GAG AAA CTG ACT GCT GAC CCC GAC AGT GAA GTG GCT ACT ACA AGT Ctc CCG GGT GTC ACT
 E   K   L   T   A   D   P   D   S   E   V   A   T   T   S   L   P   G   V   T
841/281                                 871/291
CAT GTG CCC GCT AGG AAG ATG CGC CTG ACT GTC CCG TGT CGT GCC CTC ACC TGT GCC CAT
 H   V   P   A   R   K   M   R   L   T   V   P   C   R   A   L   T   C   A   H
```

FIG. 11-2

```
901/301                                 931/311
CTG AGT TTC GAT GCT GCC CTT TAT CTA CAG ATG AAT GAG AAG AAG CCG ACA TGG ACC
 L   Q   S   F   D   A   A   L   Y   L   Q   M   N   E   K   K   P   T   W   T
961/321                                 991/331
TGT CCT GTG TGT GAC AAG AAG GCT CCC TAT Gaa TCG CTG ATT ATT GAT GGT TTA TTC ATG
 C   P   V   C   D   K   K   A   P   Y   E   S   L   I   I   D   G   L   F   M
1021/341                      ↓          1051/351
GAA ATT CTT AAT TCC TGT TCG GAT TGT GAT Gag ATC CAG TTC ATG GAA GAT GGA TCC TGG
 E   I   L   N   S   C   S   D   C   D   E   I   Q   F   M   E   D   G   S   W
1081/361                                1111/371
TGT CCG ATG AAA CCC AAG AAG GAG GcA TCA GAG GTT TGC CCC ccg cca ggg tat ggg ctg
 C   P   M   K   P   K   K   E   A   S   E   V   C   P   P   P   G   Y   G   L
1141/381                                1171/391
gat ggt ctc cag tac agc gca gtc cag gag gga att cag cca gag agt aag aag agg gtc
 D   G   L   Q   Y   S   A   V   Q   E   G   I   Q   P   E   S   K   K   R   V
1201/401                                1231/411
gaa gtc att gac ttg acc atc gaa agc tca tca gat gag gag gat ttg ccc ccc acc aag
 E   V   I   D   L   T   I   E   S   S   S   D   E   E   D   L   P   P   T   K
1261/421                                1291/431
aag cag tgc Tct gtc acC tCa gcg gcc att cca gcC ctt ttG gga agc aaa gga gTc ctg
 K   Q   C   S   V   T   S   A   A   I   P   A   L   L   G   S   K   G   V   L
1321/441                                1351/451
acA tCt ggt cac cag cca tct tcg gtg Ctg cgg agC cct gca atg ggc aca Ttg ggc agt
 T   S   G   H   Q   P   S   S   V   L   R   S   P   A   M   G   T   L   G   S
1381/461                                1411/471
gat tTC ctg tCt agt ctc ccg gta cat gag tac cca cct gCc ttc cca Ctg ggg gCt gac
 D   F   L   S   S   L   P   V   H   E   Y   P   P   A   F   P   L   G   A   D
1441/481                                1471/491
atc caa ggt tta gat tTa ttt tCt ttc ctt cag aCt gag agt cag cag tac ggc cct tca
 I   Q   G   L   D   L   F   S   F   L   Q   T   E   S   Q   Q   Y   G   P   S
1501/501                                1531/511
gtt atc atC tcg cta gat gaa cag gac acc ttg gGc cat ttC Ttc cag taC cgg ggg acC
 V   I   I   S   L   D   E   Q   D   T   L   G   H   F   F   Q   Y   R   G   T
1561/521                                1591/531
cct tcc cac ttc ctg ggc cca Ctg gcc ccc aca ctg ggg agc tgt cac ggc agt tcc act
 P   S   H   F   L   G   P   L   A   P   T   L   G   S   C   H   G   S   S   T
1621/541                                1651/551
cca gcg ccc cct cct ggt cGT GTC AGC AGC ATT GTG GCT CCT GGG AGC TCC TTG Agg GAA
 P   A   P   P   P   G   R   V   S   S   I   V   A   P   G   S   S   L   R   E
1681/561                                1711/571
GGG CAT GGA GGA Ccc CTG CCT TCA GGT Ccc TCT TTG ACT GGC TGT CGG TCA GAC GTC ATT
 G   H   G   G   P   L   P   S   G   P   S   L   T   G   C   R   S   D   V   I
1741/581
TCC TTG GAC TGA
 S   L   D   *
```

PIAS MOLECULES THAT RECOGNIZE AND BIND STAT PROTEINS AND USES THEREOF

This application is the national stage under 35 U.S.C. §371 of international application number PCT/US98/25316, filed Nov. 27, 1998, which claims the benefit of U.S. provisional patent application Nos. 60/069,251, filed Nov. 28, 1997, and 60/095,950, filed Aug. 10, 1998.

Throughout this application various publications are referenced. The disclosures of these publications in their entireties are hereby incorporated by reference into this application in order to describe more fully the state of the art to which this invention pertains.

FIELD OF THE INVENTION

The invention is directed to novel protein inhibitors of activated STAT (PIAS) and methods for making and using such proteins.

BACKGROUND OF THE INVENTION

Activation of early response genes by interferons (IFNs) and other cytokines requires tyrosine phosphorylation of a family of transcription factors termed signal transducer and activator of transcription (STAT) proteins. STAT proteins relay signals from activated cell surface receptors directly to the nucleus and have been demonstrated to play a critical role in gene induction by a variety of hemopoietic cytokines and hormones.

The STAT protein is activated by the gp130 family of cytokines, e.g., the interleukin 6 (IL6) family of cytokines, epidermal growth factor, and leptin. Tyrosine-phosphorylated STAT3 binds to a specific DNA sequence in its target genes (Zhong et al. (1994); Akira et al. (1994)) and participates in signal transduction pathways activated by the IL6 family of cytokines and by epidermal growth factor (Zhong et al. (1995); Akira et al. (1994)). STAT3 is also activated in cells treated with leptin, a growth hormone that functions in regulating food intake and energy expenditure (Zhang et al. (1994)). Targeted disruption of the mouse gene encoding STAT3 leads to early embryonic lethality (Takeda et al. (1997)). Like other members of the STAT family, STAT3 becomes tyrosine phosphorylated by Janus kinases (JAKs). Phosphorylated STAT3 then forms a dimer and translocates into the nucleus to activate specific genes (Darnell et al. (1994)).

The invention relates to a family of protein inhibitors of activated STAT (PIAS) molecules that directly inhibit STAT function. This family includes but is not limited to, PIAS1, PIAS3, PIASxα, PIASxβ, and PIASy. Sequence analysis indicates that human PIAS1 is almost identical to a previously reported human protein named GBP (Gu/RH-II binding protein) (Shuai et al. Nature (1993)). However, GBP lacks 9 amino acid residues when compared with PIAS1. Further, GBP does not function as an inhibitor of STAT but was identified as a putative interaction protein of Gu/RNA helicase II.

SUMMARY OF THE INVENTION

This invention includes novel PIAS molecules that are STAT binding molecules (e.g., STAT1 and STAT3). The binding of PIAS molecules to STAT indicates that STAT signaling pathways can be suppressed at multiple steps, in a general or specific manner. It seems that the overall strength of STAT signaling for a given cell type may be largely affected by the relative level of STAT protein and PIAS expression. Therefore, these molecules can be used for the detection and treatment of diseases associated with STAT mediated cellular responses.

BRIEF DESCRIPTION OF THE FIGURES

FIGS. 1a and 1b provides the primary sequence and expression of PIAS3 and a photograph of a gel (northern blot) showing expression of PIAS3 mRNA in human tissues, respectively SEQ ID NO:1.

FIGS. 4a-4c are bar graphs showing the effect of PIAS3 on STAT-mediated gene activation.

FIGS. 5a-b are a sequence comparison of the PIAS family of proteins including mPIAS3, hPIAS3, hPIAS1, mPIAS1, hPIASxα, hPIASxβ, and hPIASy.

FIGS. 8a-e are photographs showing the specificity of PIAS-STAT interaction.

FIGS. 9a-b are photographs showing phosphorylation on Tyr-701 of STAT1 is required for PIAS1-STAT1 interaction.

FIG. 10 is the amino acid and nucleic acid sequences of murine PIAS1 having a mutation at amino acid position 374 (Cys→Ser) SEQ ID NO:10; SEQ ID NO:11.

FIG. 11 is the amino acid and nucleic acid sequences of murine PIAS3 having a mutation at amino acid position 349 (Cys→Ser) SEQ ID NO:12; SEQ ID NO:13.

DETAILED DESCRIPTION OF THE INVENTION

Proteins of the Invention

Figure 2B:
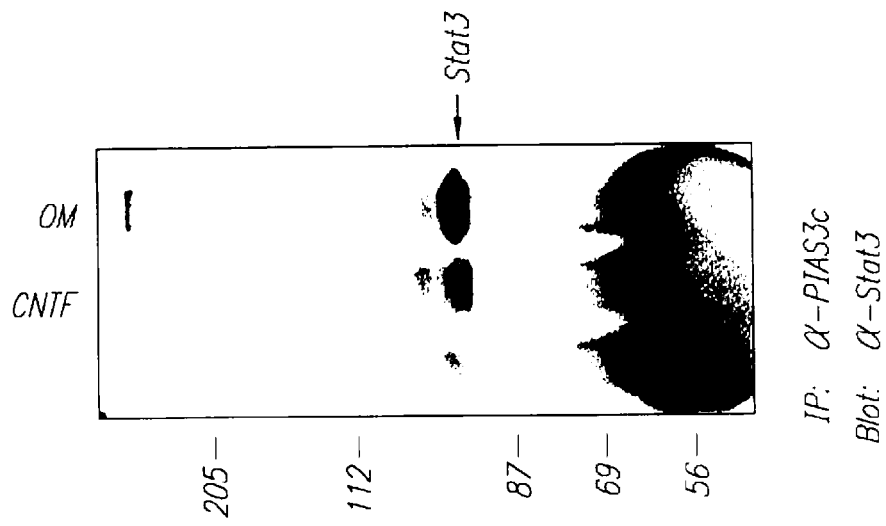
FIGS. 2a and 2b are photographs of protein immunoblots showing the in vivo interaction of PIAS3 with STAT3.

The invention relates to the PIAS family of proteins. PIAS molecules bind STAT proteins. Typically, the STAT so bound is phosphorylated and the phosphorylation (e.g., tyrosine phosphorylation) is cytokine induced.

In some embodiments, a PIAS molecule will specifically bind a member of the STAT family of proteins but not another. For example, the invention provides isolated PIAS molecules that bind and inhibit STAT1 but do not bind STAT3. By birding STAT1, these proteins block the DNA binding activity of STAT1 thereby resulting in the inhibition of STAT1 mediated gene activation. In another example, the invention provides isolated PIAS molecules that bind and inhibit STAT3 but do not bind STAT1. By binding STAT3, these proteins block the DNA binding activity of STAT3 thereby resulting in the inhibition of STAT3 mediated gene activation.

PIAS molecules described herein include PIAS from any species, e.g., mammalian, including bovine, ovine, porcine, murine, equine and human. PIAS molecules may be in a naturally occurring form or from any source whether natural, synthetic, semi-synthetic or recombinant. PIAS molecules can be embodied in many forms, preferably, in a purified or isolated form. PIAS molecules include those embodiments having the sequences disclosed herein including homologues, isoforms, allelic variants and conservative substitution mutants thereof that have STAT binding activity and can be isolated/generated without undue experimentation following the methods outlined below. For the sake of convenience, all PIAS molecules will be collectively referred to as the PIAS molecules, the proteins of the invention, or PIAS.

Particular embodiments of the PIAS family of proteins include but are not limited to PIAS1 and PIAS3.

PIAS1 binds and inhibits STAT1 but does not bind STAT3. By binding STAT1, PIAS1 blocks the DNA-binding activity of STAT1 thereby resulting in the inhibition of STAT1 mediated gene activation. STAT1 can be in the form of a homodimer or a heterodimer. Additionally, STAT1 can be STAT1 (alpha) or STAT1-β. Human PIAS1 (hPIAS1) has the sequence shown in FIG. 5. Murine PIAS1 (mPIAS1) has the sequence shown in FIG. 5. Included within the scope of the present invention are alleles (or allelic variants) of PIAS1. As used herein, an allele is an alternative form of PIAS1. Alleles result from a mutation, i.e., a change in the nucleic acid sequence and generally produce altered mRNAs or proteins whose structure of function may or may not be altered.

PIAS3 binds and inhibits STAT3 but does not recognize and bind STAT1. By binding STAT3, these proteins block the DNA-binding activity of STAT3 and STAT3 mediated cellular responses, e.g., STAT3 and IL6 mediated cellular responses. Blocking the DNA-binding activity of STAT3 results in the inhibition of a STAT3 transactivating/signaling complex. STAT3 can be in the form of a homodimer or heterodimer. Additionally, the STAT3 can be STAT3(alpha) or STAT3-β.

Figure 5B:
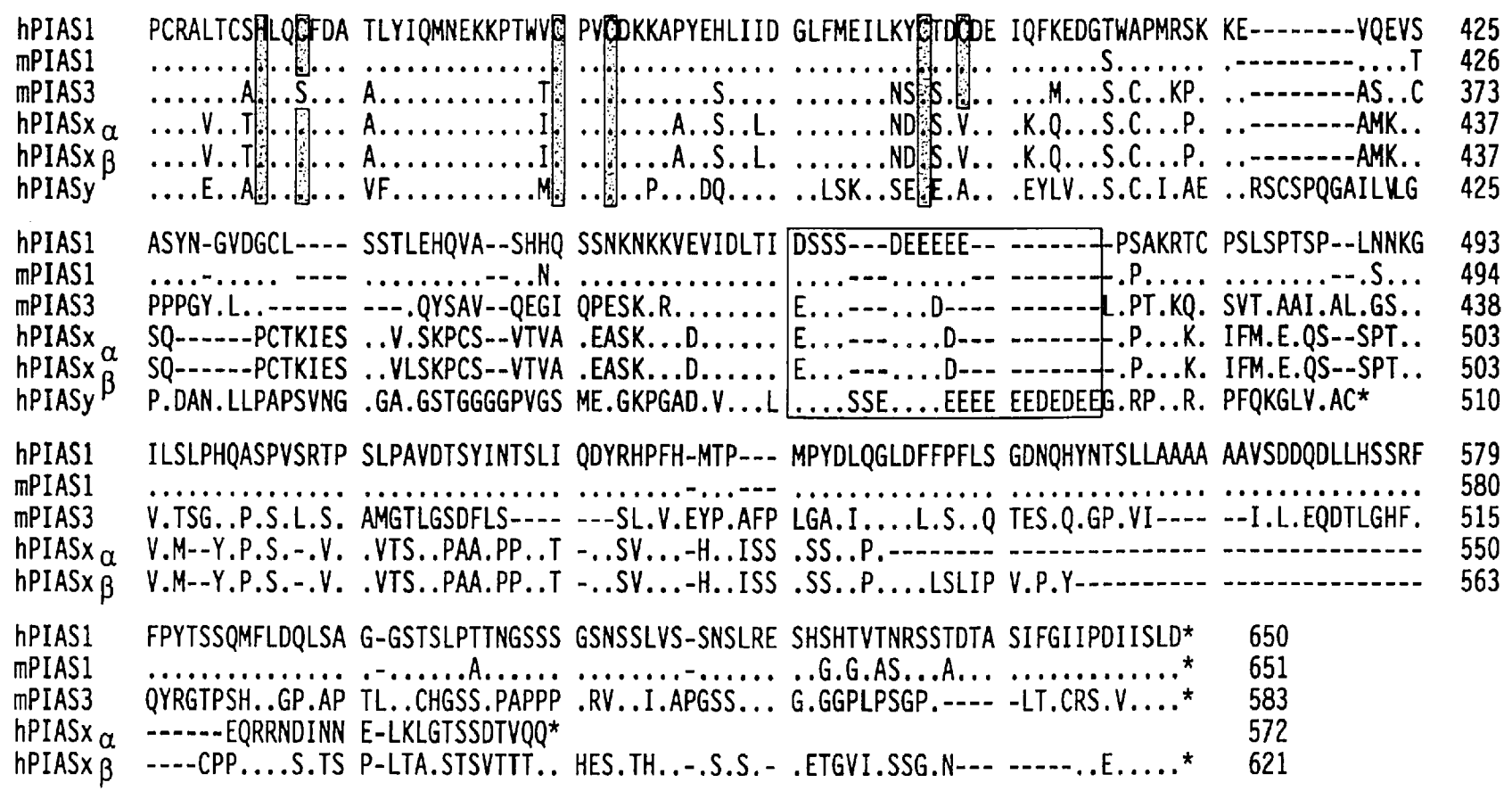

One embodiment of PIAS3 proteins is murine PIAS3 (mPIAS3) having the sequence shown in FIG. 5. Another embodiment of PIAS3 proteins is human PIAS3 (hPIAS3) having the sequence shown in FIG. 5. Included within the scope of the present invention are alleles of PIAS3.

Another embodiment the PIAS molecule is PIASxα. Human PIASxα (hPIASxα) has the sequence shown in FIG. 5.

A further embodiment of the PIAS molecules is PIASxβ. Human PIASxβ (hPIASxβ) has the sequence shown in FIG. 5.

Also, an additional embodiment of the PIAS molecules is PIASy. Human PIASy (hPIASy) has the sequence shown in FIG. 5.

In addition to allelic variants of PIAS molecules, the invention also encompasses conservative substitution mutants of PIAS molecules. For example, changes to the primary amino acid sequence of the PIAS molecules are possible so long as the resulting protein maintains the ability to function as a specific inhibitor of STAT protein (e.g., FIGS. 10 and 11). Changes include amino acid substitutions. Amino acid substitutions include, but are not necessarily limited to, amino acid substitutions known in the art as "conservative". For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa.

Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments and are encompassed by the invention.

The PIAS family of proteins, e.g., the PIAS1 and PIAS3 proteins discussed herein, exhibit significant homology (over 50%) with each other. Even more significant homology (over 70%) is found when comparing the area n-terminus to the putative zinc binding motif between the PIAS1 and PIAS3 members.

PIAS molecules have several highly conserved domains, including a putative zinc binding motif present and a highly acidic region (FIG. 5). The COOH-terminal regions of PIAS molecules are the least conserved. For example, PIASxα and PIASxβ are identical, except in their COOH terminal regions.

The invention further provides portions of the PIAS molecules of the present invention. As used herein, a portion of a PIAS molecule refers to a small portion of the entire PIAS sequence. Preferably, it is a portion or the entire area of the N-terminal domain of PIAS, i.e., the portion of PIAS that can inhibit STAT. Typically, it is the area located N-terminal to the zinc binding motif of PIAS. A portion of the N-terminal domain of PIAS includes, but is not limited to, amino acid positions 1 to 425 of PIAS1 and PIAS3; amino acid positions 1-133 of PIAS1 and PIAS3, and amino acid positions 50-168 of PIAS1 and PIAS3). The size of the portion will be determined by its intended use.

For example, if the portion is to be used as an immunogen, then a fragment length is chosen so as to generate antibodies directed against that portion of PIAS. Portions of PIAS that are particularly useful can be readily identified from the entire PIAS sequence using art-known methods.

PIAS Antibodies

The invention further provides antibodies that bind to PIAS. The most preferred antibodies will selectively bind to PIAS and will not bind (or will bind weakly) to non-PIAS. Anti-PIAS antibodies that are particularly contemplated include monoclonal and polyclonal antibodies as well as fragments containing the antigen binding domain and/or one or more complement determining regions of these antibodies.

In one embodiment, the PIAS antibodies specifically bind to the area n-terminal to the zinc binding motif of PIAS. In other embodiments, the PIAS antibodies specifically bind to other domains of PIAS. As will be understood by those skilled in the art, the regions or epitopes of PIAS to which an antibody is directed may vary with the intended application.

The invention also encompasses antibody fragments which specifically recognize PIAS. As used herein, an antibody fragment is defined as at least a portion of the variable region of the immunoglobulin molecule which binds to its target, i.e., the antigen binding region. Some of the constant region of the immunoglobulin may be included.

PIAS antibodies may also be used in methods for purifying PIAS and peptides and for isolating PIAS homologues and related molecules. For example, in one embodiment, the method of purifying PIAS comprises incubating a PIAS antibody, which has been coupled to a solid matrix, with a lysate or other solution containing PIAS under conditions which permit the PIAS antibody to bind to PIAS, washing the solid matrix to eliminate impurities; and eluting the PIAS from the coupled antibody.

Other uses of the PIAS antibodies of the invention include generating anti-idiotypic antibodies that mimic PIAS.

Various methods for the preparation of antibodies are well known in the art. For example, antibodies may be prepared by immunizing a suitable mammalian host using PIAS, peptide, or fragment, in isolated or immunoconjugated form (Harlow, Antibodies, Cold Spring Harbor Press, NY (1989)). In addition, fusion proteins of PIAS may also be made and used, such as a PIAS GST-fusion protein. One embodiment of a PIAS fusion protein would be a N-terminal PIAS protein (e.g., from amino acid positions 1 to 425 or 1 to 133 (FIG. 5)). Cells expressing or overexpressing PIAS may also be used for immunizations. Similarly, any cell engineered to express PIAS may be used. This strategy may result in the production of monoclonal antibodies with enhanced capacities for recognizing endogenous PIAS.

The amino acid sequence of PIAS presented herein may be used to select specific regions of PIAS for generating antibodies. For example, hydrophobicity and hydrophilicity analyses of the PIAS amino acid sequence may be used to identify hydrophilic regions in the PIAS structure. Further, a portion of the N-terminal region of PIAS is required for the inhibiting STAT, therefore, such portions can be used to generate fusion proteins in methods for making antibodies and other diagnostic or therapeutic applications. Further still, regions of PIAS that show immunogenic structure, as well as other regions and domains, can readily be identified using various other methods known in the art; such as Chou-Fasman, Garnier-Robson, Kyte-Doolittle, Eisenberg, Karplus-Schultz or Jameson-Wolf analysis. For example, it appears that the N-terminus of PIAS (e.g., the area located N-terminus of the zinc binding motif) to binds STAT. Fragments containing these residues may be particularly suited in generating specific classes of anti-PIAS antibodies.

Methods for preparing a protein for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a PIAS immunogen is conducted generally by injection over a suitable time period and with use of a suitable adjuvant, as is generally understood in the art. During the immunization schedule, titers of antibodies can be taken to determine adequacy of antibody formation.

While the polyclonal antisera produced in this way may be satisfactory for some applications, for pharmaceutical compositions, monoclonal antibody preparations are preferred. Immortalized cell lines which secrete a desired monoclonal antibody may be prepared using the standard method of Kohler and Milstein or modifications which effect immortalization of lymphocytes or spleen cells, as is generally known. The immortalized cell lines secreting the desired antibodies are screened by immunoassay in which the antigen is PIAS or fragment thereof. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of PIAS can also be produced in the context of chimeric or CDR grafted antibodies of multiple species origin.

The antibody or fragment thereof of the invention may be labeled with a detectable marker or conjugated to a second molecule, such as a cytotoxic agent, and used for targeting the second molecule to an PIAS positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624-2636). Examples of cytotoxic agents include, but are not limited to ricin, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, ricin, abrin, and glucocorticoid and other chemotherapeutic agents, as well as radioisotopes. Suitable detectable markers include, but are not limited to, a radioisotope, a fluorescent compound, a bioluminescent compound, chemiluminescent compound, a metal chelator or an enzyme.

PIAS antibodies conjugated with toxic agents, such as ricin, as well as unconjugated antibodies are encompassed by the invention. Techniques for conjugating therapeutic agents to antibodies are well known (see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); and Thorpe et al., "The Preparation And Cytotoxic Properties Of Antibody-Toxin Conjugates", *Immunol. Rev.*, 2:119-58 (1982)).

Nucleic Acid Molecules of the Invention

The present invention provides nucleic acid sequences encoding the STAT-binding proteins of the invention. The nucleic acid sequences can be DNA, RNA, DNA/RNA hybrid, and related molecules, nucleic acid molecules complementary to the PIAS coding sequence or a part thereof, and those which hybridize to the PIAS gene or to PIAS-encoding nucleic acids. Particularly preferred nucleic acid molecules will have a nucleotide sequence substantially identical to or complementary to the human or murine DNA sequences herein disclosed. Specifically contemplated are genomic DNA, cDNAs, ribozymes, and antisense molecules, as well as nucleic acids based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the herein described PIAS sequences. For convenience, PIAS-encoding nucleic acid molecules will be refereed to herein as PIAS-encoding nucleic acid molecules, PIAS genes, or PIAS sequences.

Embodiments of the PIAS-encoding nucleic acid molecules of the invention include primers, which allow the specific amplification of nucleic acid molecules of the invention or of any specific parts thereof, and probes that selectively or specifically hybridize to nucleic acid molecules of the invention or to any part thereof. The nucleic acid probes can be labeled with a detectable marker. Examples of a detectable marker include, but are not limited to, a radioisotope, a fluorescent compound, a bioluminescent compound, a chemiluminescent compound, a metal chelator or an enzyme. Such labeled probes can be used to diagnose the presence of a PIAS protein as a means for detecting cells expressing a PIAS protein. Technologies for generating DNA and RNA probes are well known.

As used herein, a nucleic acid molecule is said to be "isolated" when the nucleic acid molecule is substantially separated from contaminant nucleic acid molecules that encode polypeptides other than PIAS. A skilled artisan can readily employ nucleic acid isolation procedures to obtain an isolated PIAS-encoding nucleic acid molecule.

The invention further provides fragments of the PIAS-encoding nucleic acid molecules of the present invention. As used herein, a fragment of a PIAS-encoding nucleic acid molecule refers to a small portion of the entire PIAS-encoding sequence. The size of the fragment will be determined by its intended use. For example, if the fragment is to be used as a nucleic acid probe or PCR primer, then the fragment length is chosen so as to obtain a relatively small number of false positives during probing/priming. Fragments of PIAS that are particularly useful as selective hybridization probes or PCR primers can be readily identified from the entire PIAS sequence using art-known methods.

Additionally, the invention provides vectors having the nucleic acid sequences above. Also provided are host-vector systems comprising vectors of the invention transfected into a compatible host cell and expressing PIAS (Sambrook et al., *Molecular Cloning* (1989).

The host cell can be either prokaryotic or eukaryotic. Eukaryotic cells useful for expression of a PIAS protein are not limited, so long as the cell line is compatible with cell culture methods and compatible with the propagation of the expression vector and expression of a PIAS gene. Eukaryotic host cells include, but are not limited to, yeast, insect and mammalian cells, preferably vertebrate cells such as those from a mouse, rat, monkey or human cell line. Any prokaryotic host can be used to express a PIAS-encoding DNA molecule, e.g., *E. coli.*

Transformation of appropriate cell hosts with a nucleic acid molecule of the present invention is accomplished by well known methods that typically depend on the type of vector used and host system employed. With regard to transformation of prokaryotic host cells, electroporation and salt treatment methods are typically employed, see, for example, Cohen et al., *Proc Acad Sci USA* (1972) 69:2110; and Maniatis et al, *Molecular Cloning, A Laboratory Manual*, Cold Spring Harbor Laboratory, Cold Spring Harbor, N.Y. (1982). With regard to transformation of vertebrate cells with vectors containing DNAs, electroporation, cationic lipid or salt treatment methods are typically employed, see, for example, Graham et al., *Virol* (1973) 52:456; Wigler et al., *Proc Natl Acad Sci USA* (1979) 76:1373-76.

Successfully transformed cells, i.e., cells that contain a nucleic acid molecule of the present invention, can be identified by well known techniques. For example, cells resulting from the introduction of a nucleic acid molecule of the present invention can be cloned to produce single colonies. Cells from those colonies can be ha-vested, lysed and their DNA content examined for the presence of the rDNA using a method such as that described by Southern, *J Mol Biol* (1975) 98:503, or Berent et al., *Biotech* (1985) 3:208 or the proteins produced from the cell assayed via an immunological method.

Methods of the Invention

Further provided are methods for producing PIAS molecules of the invention.

These methods include recombinant methods and production methods known in the art such as growing cells containing any one of the host vector systems of the invention so as to produce the PIAS molecules in the host and recovering the protein so produced.

For example, a nucleic acid molecule is obtained that encodes a PIAS protein or a fragment thereof. The PIAS-encoding nucleic acid molecule is then preferably placed in an operable linkage with suitable control sequences, as described above, to generate an expression unit containing the PIAS-encoding sequence. The expression unit is used to transform a suitable host and the transformed host is cultured under conditions that allow the production of the PIAS protein. Optionally the PIAS protein is isolated from the medium or from the cells; recovery and purification of the protein may not be necessary in some instances where some impurities may be tolerated.

Each of the foregoing steps may be done in a variety of ways. For example, the desired coding sequences may be obtained from genomic fragments and used directly in an appropriate host. The construction of expression vectors that are operable in a variety of hosts is accomplished using an appropriate combination of replicons and control sequences. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with PIAS-encoding sequences to produce a PIAS protein.

Additionally, the invention provides methods for using the proteins of the invention.

For example, the invention provides methods for blocking (or inhibiting) the activity (e.g., DNA-binding activity) of STAT proteins (e.g., STAT1 or STAT3). In one embodiment, the method comprises contacting a PIAS molecule or portion thereof that bind a STAT protein (e.g. so that a PIAS/STAT complex is formed) so as to block the activity (e.g., DNA-binding activity) of the STAT protein so contacted. Further, STAT contacted with PIAS can prevent STAT from activating genes (gene transcription) controlled by STAT. These genes controlled by STAT include but are not limited to CFOS and Fc(γ) receptor.

The invention additionally provides methods for regulating an IFN-associated immune response mediated by STAT. The immune response includes an anti-viral response mediated by IFN, anti-tumor response mediated by IFN, and/or B and T cell responses mediated by IFN. In one embodiment of the invention, the method comprises contacting STAT positive cells (e.g., STAT1 positive cells) with a PIAS molecule (e.g., any of the PIAS1 proteins of the invention) and blocking the DNA-binding activity of STAT.

Blocking the DNA-binding activity of STAT prevents STAT from activating genes that regulates the IFN-associated immune response.

With respect to the methods of the invention, the most effective mode of administration and dosage regimen for the molecules of the present invention depends upon the severity and course of the disease, the subject's health and response to treatment and the judgment of the treating physician. Accordingly, the dosages of the molecules should be titrated to the individual subject.

For example, the interrelationship of dosages for animals of various sizes and species and humans based on mg/m² of surface area is described by Ferrite, E. J., et al. (Quantitative Comparison of Toxicity of Anticancer Agents in Mouse, Rat, Hamster, Dog, Monkey and Man. Cancer Chemother, Rep., 50, No. 4, 219-244, May 1966).

Adjustments in the dosage regimen can be made to optimize the response. Doses can be divided and administered on a daily basis or the dose can be reduced proportionally depending upon the situation. For example, several divided doses can be administered daily or the dose can be proportionally reduced as indicated by the specific therapeutic situation.

The following example is presented to illustrate the present invention and to assist one of ordinary skill in making and using the same. The example is not intended in anyway to otherwise limit the scope of the invention.

EXAMPLE 1

This example describes the identification of PIAS3.

PIAS1 which can specifically interact with STAT1 was cloned using the yeast two-hybrid assays (Taniguchi et al. (1995). The expressed sequence tag (EST) database was searched for other PIAS family members (GENBANK). The database search was done with the Baylor College of Medicine Search Launcher. A human EST clone encoding a polypeptide related to the COOH-terminal portion of PIAS1 was identified. The name of this EST clone was HE6WCR27 (GenBank accession number H58757).

Using PIAS1 so cloned, a full-length cDNA of murine PIAS3 was obtained containing an open reading frame of 583 amino acids by screening a mouse thymus library with the human EST clone. FIG. 1 shows the primary sequence and expression of PIAS3. In FIG. 1a, the predicted amino acid sequence of mouse PIAS3 is shown. The four cysteine residues that are predicted to form a zinc finger are underlined. In FIG. 1b, expression of PIAS3 mRNA in human tissues is shown. Human tissue blot was probed with human EST clone HE6WCR27 following manufacture's instructions.

PIAS3 protein contains a putative zinc-binding motif $[C_2—(X)_{21}—C_2]$, a feature conserved in the PIAS family (FIG. 1A). Northern (RNA) blot analysis indicated that PIAS3 is widely expressed in various human tissues (FIG. 1B). Single-letter abbreviations for the amino acid residues are as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; X, any amino acid; and Y, Tyr.

Function of PIAS3

To study the function of PIAS3 in vivo, a specific antiserum (anti-PIAS3c) was prepared to a recombinant fusion protein of glutathione S-transferase (GST) with the 79 COOH-terminal amino, acid residues of PIAS3. This antiserum detected a protein with a molecular mass of about 68 kD, the predicted size of PIAS3, in both cytoplasmic and nuclear extracts of a number of human and murine cell lines.

To identify which STAT protein interacts with PIAS3, protein extracts were prepared from murine myeloblast M1 cells, which were untreated or treated with IL6. Proteins immunoprecipitated with anti-PIAS3c were analyzed by protein immunoblot with anti-STAT3. STAT3 was present in a PIAS3 immunoprecipitate from IL6 treated M1 cells but not in an immunoprecipitate from untreated M1 cells (FIG. 2A). A reblot of the filter with anti-PIAS3c showed that similar amounts of PIAS3 were present in each lane. IL6 stimulation can induce tyrosine phosphorylation of STAT1 as well as STAT3 (Sadowski et al. (1993)). The protein blot was therefore washed and reprobed with antibody to STAT1. STAT1 was not present in PIAS3 immunoprecipitates (FIG. 2A). Furthermore, PIAS3 was not found to be associated with STAT1 in a number of cell lines treated with interferon-γ. These results indicate that PIAS3 specifically interacts with STAT3.

FIG. 2 shows the in vivo interaction of PIAS3 with STAT3. FIG. 2a shows treatment with IL6 induced the interaction of PIAS3 with STAT3. Protein extracts from M1 cells, untreated (−) or treated with IL6 for 10 min (+), were subjected to immunoprecipitation (IP) with anti-PIAS3c. The blot was probed with anti-STAT. The same blot was then reprobed with anti-PIAS3c. The filter was washed and reprobed with anti-STAT1.

STAT3 can be activated by other cytokines in the IL6 family, such as ciliary neurotrophic factor (CNTF) and oncostatin M (OM) (Akira et al. (1994)). In human HepG2 cells, STAT3 was associated with PIAS3 in cells stimulated with CNTF or OM but not in untreated cells (FIG. 2B).

Figure 2A:
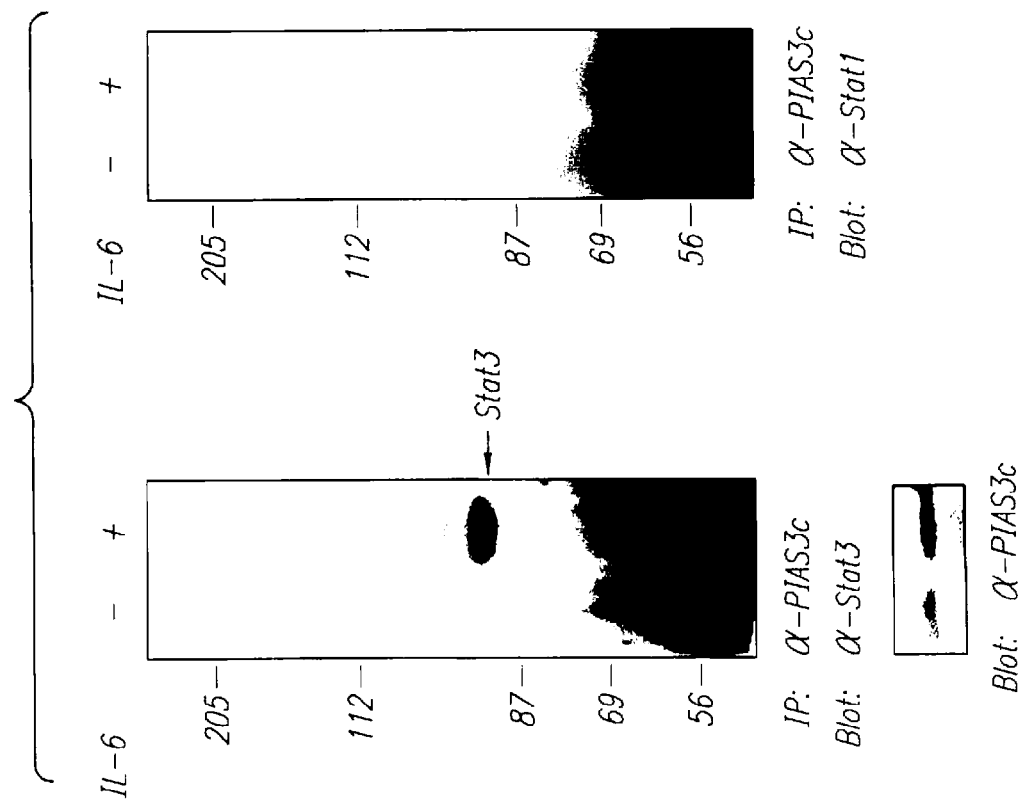

FIG. 2b shows treatment with CNTF or OM induces the interaction of PIAS3 with STAT3. Protein extracts from human HepG2 cells, untreated or treated with CNTF or OM for 10 min, were subjected to immunoprecipitation with anti-PIAS3c. The blot was probed with anti-STAT3. Whole-cell extracts were prepared with lysis buffer containing 1% Brij, 50 mM tris (pH 8), 150 mM NaCl, 1 mM dithiothreitol, 0.5 mM phenylmethylsulfonyl fluoride, leupeptin (0.5 µg/ml), aprotinin (3 µg/ml0, pepstatin (1 µg/ml), and 0.1 mM sodium vanadate. The mixture was rotated at 4° C. for 30 min and centrifuged at 13,000 g for 5 min. The supernatant was used for immunoprecipitation with anti-PIAS3c (1:100 dilution). Immunoprecipitation and protein immunoblotting were done as described.

The effect of PIAS3 on the DNA-binding activity of STAT3 was tested. Nuclear extracts from HepG2 cells were prepared and analyzed in mobility gel shift assays, with a high-affinity STAT3-binding site as the probe (Zhong et al. (1994); Sadowski et al. to (1993)). Treatment with IL6 induced the binding of three distinct gel shift complexes (Zhong et al. (1994); Sadowski et al. (1993)) corresponding to a STAT3-STAT3 homodimer, a STAT3-STAT1 heterodimer, and a STAT1-STAT1 homodimer (FIG. 3A).

A recombinant fusion protein of GST with PIAS3 (GST-PIAS3) was prepared and purified and added (in 20- to 200-ng quantities) to IL6-treated HepG2 nuclear extracts. GST-PIAS3 (100 ng) completely inhibited the DNA-binding activity of the STAT3-STAT3 homodimer and the STAT3-STAT1 heterodimer (FIG. 3A) but had no effect on the DNA-binding ability of the STAT1-STAT1 homodimer. As a control, GST alone did not inhibit the DNA-binding ability of any of the three complexes. A similar inhibitory effect of PIAS3 on the DNA-binding activity of STAT3 was observed in nuclear extracts prepared from IL6-treated M1 and MCF7 cell.

To further demonstrate the specific inhibitory effect of GST-PIAS3 on STAT3, the effect of GST-PIAS3 was tested on the DNA-binding activity of nuclear factor kappa B (NF-κB). Nuclear extracts prepared from untreated MCF7 cells or MCF7 cells treated with tumor necrosis factor-α (TNF-α) were analyzed by mobility gel shift analysis with a NF-κB-binding site as the probe. TNF-α induced the formation of an NF-κB gel shift complex. The presence of either GST or GST-PIAS3 had no effect on the DNA-binding activity of NF-κB (FIG. 3B). These results demonstrate that PIAS3 can specifically inhibit the DNA-binding activity of STAT3.

Figure 3A:
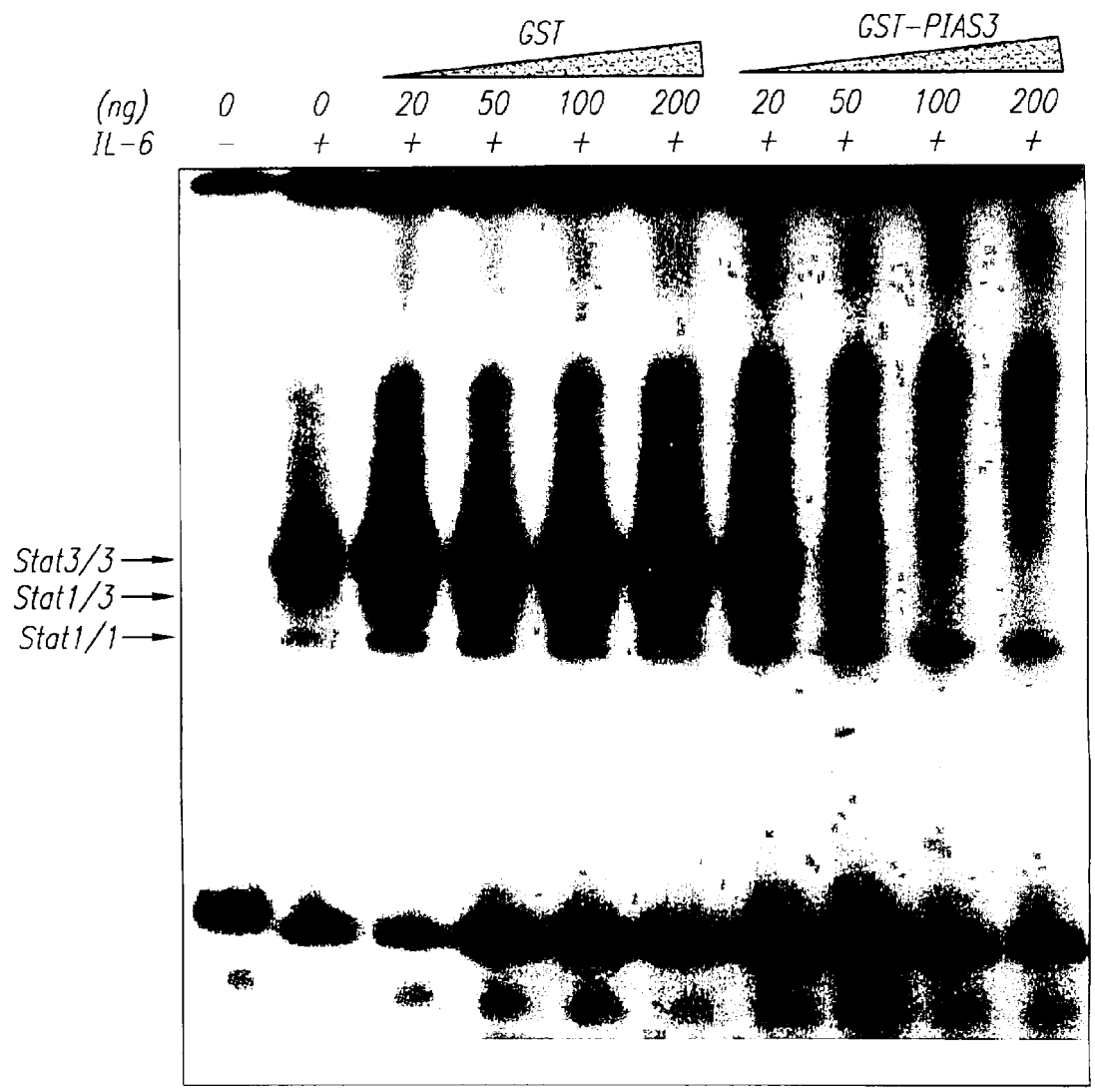
FIGS. 3a and 3b are photographs of electrophoretic mobility shift assays showing the inhibition of the DNA-binding activity of STAT3 by PIAS3.
Figure 3B:
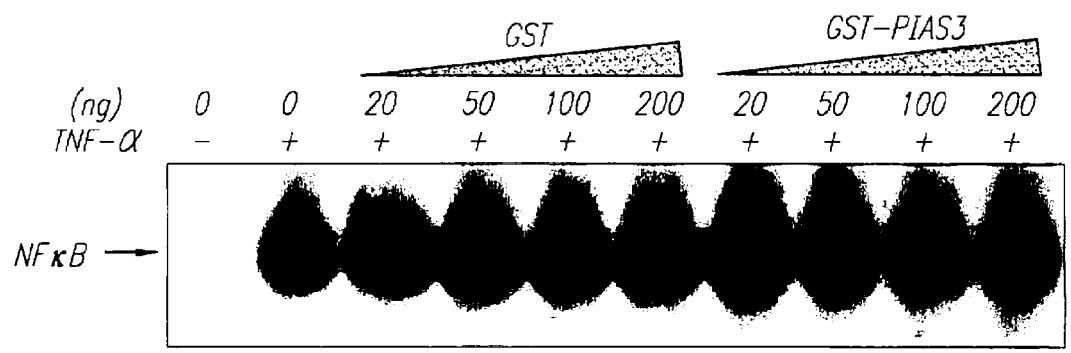

FIG. 3a/b shows the inhibition of the DNA-binding activity of STAT3 by PIAS3. FIG. 3a provides electrophoretic mobility shift assays that were performed with nuclear extracts prepared from HepG2 cells with (+) or without (−) IL6 treatment in the absence of various amounts of either GST or GST-PIAS3 proteins (20 to 200 ng) as indicated. Mobility shift assays were done as described. The probe used is a high-affinity STAT3-binding site to which both STAT1 and STAT3 can bind (Zhong et al. (1995); Leveillard et al. (1993)). STAT-1, STAT1 homodimer; STAT3-3, STAT3 homodimer; STAT1-3, STAT1 and STAT3 heterodimer.

FIG. 3b provides the same electrophoretic mobility shift assays FIG. 3a, except that nuclear extracts were prepared from MCF7 cells with (+) or without (−) TNF-α treatment. The probe was derived from the NF-κB binding site in the promoter of the NF-κB inhibitor I-κB gene (Leveillard et al. (1993)). GST-PIAS3 was constructed by insertion of the cDNA into the Sal I and Not I cloning sites of pGEX4T-1. The concentration of GST-PIAS3 was estimated on 7% SDS-polyacrylamide gel electrophoresis with various dilutions of bovine serum albumin as the standard.

To test the effect of PIAS3 on STAT3-mediated gene activation, we transiently transfected HepG2 cells with expression vectors encoding STAT3 and FLAG-tagged PIAS3. Interleukin-6 can induce the association of PIAS3 with STAT3 in HepG2 cells. A luciferase reporter construct [(4X)IRF-1] containing four copies of the STAT-binding sequence from the interferon regulatory factor-1 (IRF-1) gene was used (Wen et al. (1995)). Cotransfection of STAT3 with (4X)IRF-1 resulted in about 20-fold stimulation of luciferase expression when cells were treated with IL6 (FIG. 4A). In the presence of various amounts of PIAS3 (0.5 µg and 1 µg), STAT3-mediated induction of luciferase expression in response to IL6 stimulation was inhibited (FIG. 4A).

Luciferase assays were also performed in human embryonic 293 cells. Interferon-α (INF-α) stimulation can activate STAT3 in 293 cells (Wen et al. (1995)). Cells cotransfected with STAT3 and (4X)IRF-1 reporter construct showed a 150-fold increase of luciferase expression in response to INF-α (FIG. 4B). In the presence of PIAS3 (1 µg), however, the IFN-α induced, STAT3-dependent gene activation was almost completely inhibited.

PIAS3 (1 µg) had no such inhibitory effect on STAT1-mediated transcription activated in response to IFN-α (FIG. 4C). These results are in accord with the data that PIAS3 does not interact with STAT1 or inhibit its DNA-binding activity and indicate that PIAS3 is a specific inhibitor of STAT3-mediated gene activation.

FIG. 4 shows the effect of PIAS3 on STAT-mediated gene activation. Panel A of FIG. 4 shows inhibition of STAT3-mediated gene activation in response to IL6. HepG2 cells were transiently transfected with (4X)IRF-1 luciferase reporter construct together with an empty expression vector, STAT3, or various amount of FLAG-PIAS3 vectors, alone or in combination as indicated. Twenty-four hours after transfection, cultures were either left untreated (open columns) or treated with IL6 (10 ng/ml) for 6 hours (solid columns), and cell extracts were prepared and measured for luciferase activity.

Panel B shows inhibition of STAT3-mediated gene activation in response to IFN-α. Human 293 cells were transfected with (4X)IRF-1 luciferase reporter construct together with STAT3 or PIAS3 (or both) as indicated. Twenty-four hours after transfection, cells were left untreated (open columns) or treated with IFN-α (5 ng/ml) for 6 hours (solid columns), and luciferase activity was determined.

Panel C shows the effect of PIAS3 on STAT1-mediated gene activation. Panel C is the same as panel (B) except that STAT3 was replaced with STAT1 in cotransfection assays. FLAG-PIAS3 was constructed by insertion of the cDNA into the Sal I and Hind III sites of pCMV5-FLAG. HepG2 cells were transfected by modified calcium phosphate method. Cells were grown in Dulbecco's modified Eagle's medium containing 5% fetal bovine serum and 25-hydroxycholesterol (2.5 µg/ml) and were maintained at 350° C. and 3% $CO_2$ for 3.5 hours during transfection. 293 cells were transfected by the calcium phosphate method (Shuai et al. (1994)). Data shown are taken from one representative experiment and was repeated at least three times. The relative luciferase units were corrected relative to the expression of β-galactosidase.

EXAMPLE 2

This example describes the identification, isolation, and characterization of PIAS1. PIASγ, PIASxα, and PIASxβ are also described.

In this Example, the yeast two-hybrid method was used to identify additional proteins which can interact with STAT1, (Taniguchi et al. (1995)). By EST database searching and library screening, the murine PIAS1 as well as four related clones that encode putative new members of the PIAS family were identified (Meraz et al. (1996)).

The murine full length PIAS1 cDNA was obtained by sequencing EST clone #930725 (GENBANK). EST clone #785675 was used to screen a human testis library to obtain PIASxα and PIASxβ. EST clone #59244 was sequenced and identified as PIASγ.

STAT1β fused to LexA was used as a bait to screen a yeast interaction library prepared from human JY112 B cells [D. D. Chang, C. Wong, H. Smith, J. Liu, JCB, 138, 1149 (1997)]. Fifty positive clones were identified from $3 \times 10^6$ primary transformants. Of these clones, 40 were partial-length cDNAs encoding the COOH-terminal 313 amino acids of PIAS1. A longer cDNA clone which was obtained by screening a human K562 cDNA library was fused with EST clone #301840 to generate the full length human PIAS1 cDNA.

FIG. 5 provides a sequence comparison of the PIAS family of proteins. The predicted amino-acid sequences of PIAS1, PIAS3, PIASxα, PIASxβ, and PIASγ are shown. h: human; m: mouse. Cysteine and histidine residues that are predicted to form a zinc finger (also referred to herein as the zinc binding motif) are shaded. The conserved acidic region is boxed. Dots indicate amino acid identity. The nucleotide sequences of each of these genes has been deposited in GenBank under the accession numbers hPIAS1: AF077951;

mPIAS1: AF077950; hPIASxα: AF077953; hPIASxβ: AF077954; hPIASy: AF077952.

To test if PIAS1 is involved in regulating STAT1 activity, the effect of PIAS1 on STAT1-mediated gene activation by luciferase assays was examined. A luciferase reporter construct [(3x)Ly6] containing three copies of the STAT1-binding sequence from the murine Ly-6A/E gene was used (Shuai et al., Cell (1994); David et al., (1993)). Human 293 cells were transfected with expression vectors encoding FLAG-tagged STAT1 and PIAS1 together with [(3x)Ly6] in various combinations as indicated (FIG. 6A).

Figure 6A:
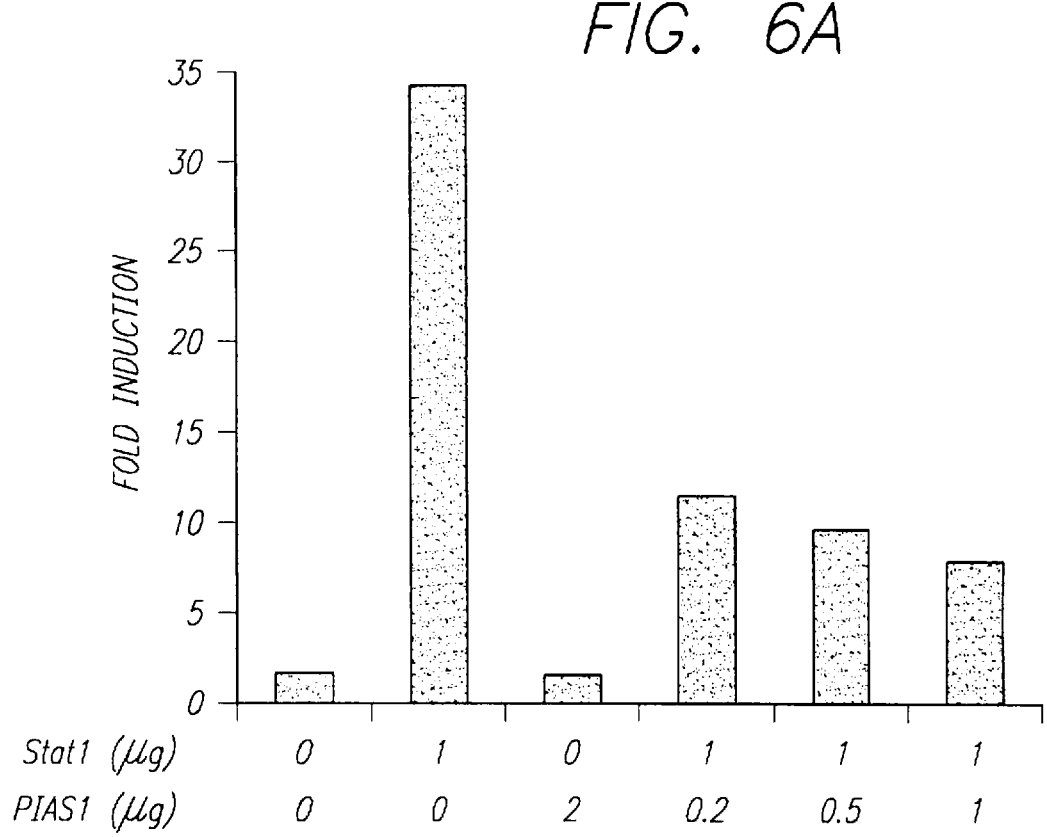
FIGS. 6a and 6b are bar graphs and photograph showing that PIAS1 inhibits STAT1-mediated gene activation.

Panel A of FIG. 6 provides Luciferase reporter assays. Human 293 cells were transiently transfected with [(3x)Ly6] luciferase reporter construct together with empty expression vector, FLAG-STAT1 or various amounts of FLAG-PIAS1 vectors, alone or in combination as indicated. Twenty four hours after transfection, cultures were either left untreated or treated with IFN-γ for 6 hours and cell extracts were prepared and measured for luciferase activity (Promega). The relative luciferase units were corrected for relative expression of β-galactosidase. Calcium phosphate was used for transfection (Shuai et al. Science (1993)). Cells cotransfected with STAT1 and [(3x)Ly6] reporter construct showed a 35-fold increase of luciferase expression in response to IFN-γ. In the presence of an increasing amount of PIAS1, the STAT1-activated luciferase expression in response to IFN-γ stimulation was dramatically inhibited (FIG. 6A).

Figure 6B:

The expression of STAT1 and PIAS1 in these transfections was confirmed by Western blot analysis of the same extracts with anti-FLAG antibody (FIG. 6B). Panel B provides the Western blot analysis. Equal amounts of protein extracts from (A) were analyzed by immunoblot with anti-FLAG (Sigma). FLAG-PIAS1 was constructed by insertion of the murine PIAS1 cDNA into the Bgl II and Sal I sites of pCMV-FLAG vector.

In contrast, neither PIAS3 nor PIASx was able to inhibit the STAT1-mediated gene activation (Durbin et al (1996); Haque et al. (1995)). These results demonstrated that PIAS1 can inhibit STAT1-mediated gene activation.

Figure 7:
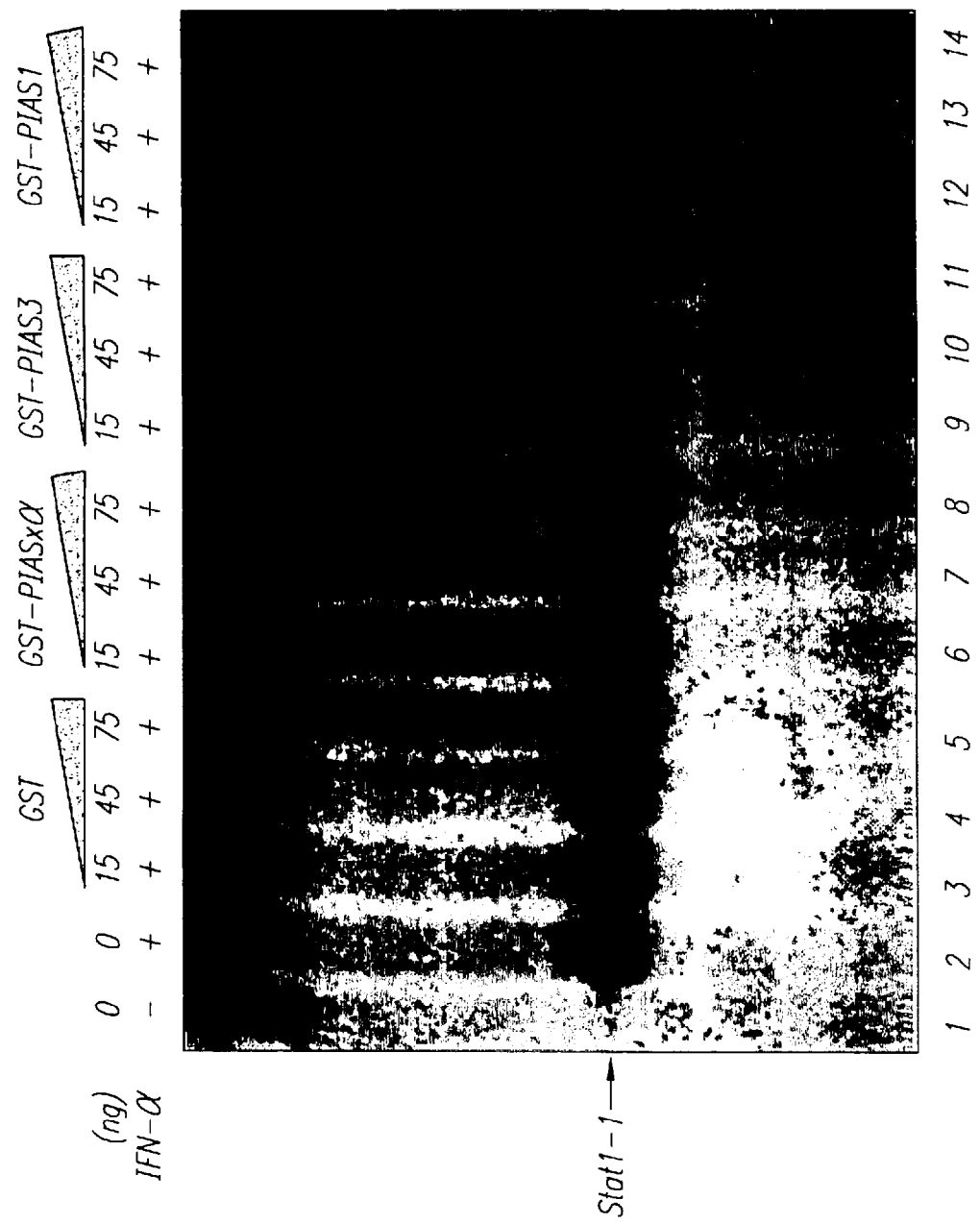
FIG. 7 is a photograph showing that PIAS1 inhibits the DNA binding activity of STAT1.

FIG. 7 demonstrates that PIAS1 inhibits the DNA binding activity of STAT1. A recombinant fusion protein of glutathione-S-transferase (GST) with PIAS1 (GST-PIAS1) was prepared and purified as well as GST-PIAS3 and GST-PIASxα. The effect of these fusion proteins on the DNA binding activity of STAT1 was tested.

Nuclear extracts from human Daudi B cells treated with IFN-α were incubated with GST or GST-PIASxα or GST-PIAS3 or GST-PIAS1 (15 to 75 ng). The mixtures were then analyzed by gel retardation assays, using the STAT1 DNA binding site as the probe (FIG. 7). GST-PIAS1 (45 ng) completely blocked the DNA binding activity of STAT1. In contrast, GST, GST-PIASxα and GST-PIAS3 had little effect on STAT1 binding. These results suggest that PIAS1 but not other PIAS molecules, can inhibit the DNA binding activity of STAT1. Electrophoretic mobility shift analysis was performed as described (Wu et al. (1997)). The probe used is a high-affinity STAT1-binding binding site (Sadowski et al. (1993)); The concentration of GST fusion proteins were estimated on 7% SDS-polyacrylamide gel electrophoresis with various dilutions of bovine serum albumin as the standard. GST-PIASxα and GST-PIAS1 constructs were prepared by insertion of human PIASxα cDNA or murine PIAS1 cDNA into the EcoRI and Not I sites of p4T-1 (Pharmacia).

The specificity of protein-protein interactions may be lost when examined in vitro or when assayed under overexpression conditions. Therefore, PIAS-STAT interactions were analyzed in vivo. A specific antiserum (anti-PIAS1n) was prepared against a GST fusion protein containing 119 amino acid residues from the NH2-terminal region of PIAS1 (amino acid 50 to 168). This antibody specifically recognized a protein with the molecular weight of 78 kDa, the predicted size of PIAS1, in a number of human and murine cell lines tested (Shuai et al. (1996)).

It was determined whether PIAS1 is associated with or bound to STAT1 in vivo. Protein extracts prepared from human Daudi B cells untreated or treated with IFN-α for 1' min were used for immunoprecipitation with anti-PIAS1n. The immunoprecipitates were then washed and analyzed by Western blot with anti-STAT1 antibody. STAT1 was present in the PIAS1 immunoprecipitate from cells treated with IFN-α but not from untreated cells (FIG. 8A). These results suggest that PIAS1 is associated with STAT1 in vivo and that the PIAS1-STAT1 interaction is dependent on ligand stimulation.

Since IFN-α also activates STAT2 (Haspel et al. (1996)), it was determined whether PIAS1 could interact with STAT2 upon IFN-α stimulation. In panel A of FIG. 8 PIAS1 interacts with STAT1 in vivo. Protein extracts from Daudi cells untreated (−) or treated (+) with IFN-γ for 15 minutes were prepared and used for immunoprecipitation with anti-PIAS1n. Immunoprecipitates were then analyzed on SDS-PAGE and the blot was probed anti-STAT1. The filter was washed and reprobed with anti-PIAS1 (lower panel).

Figure 8E:
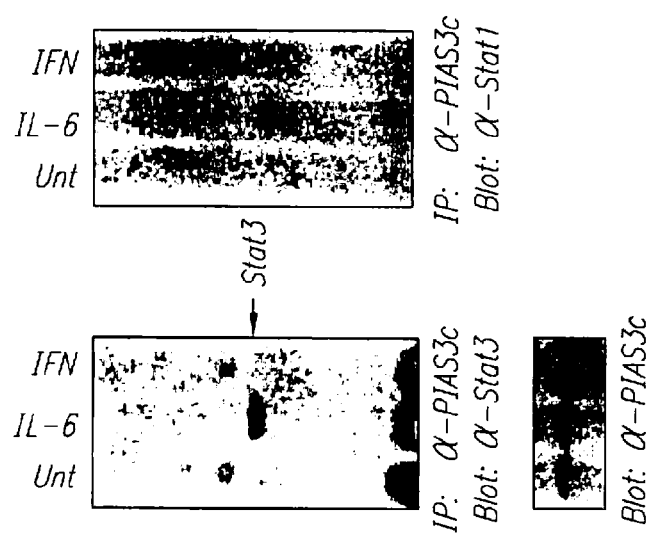
Figure 8D:
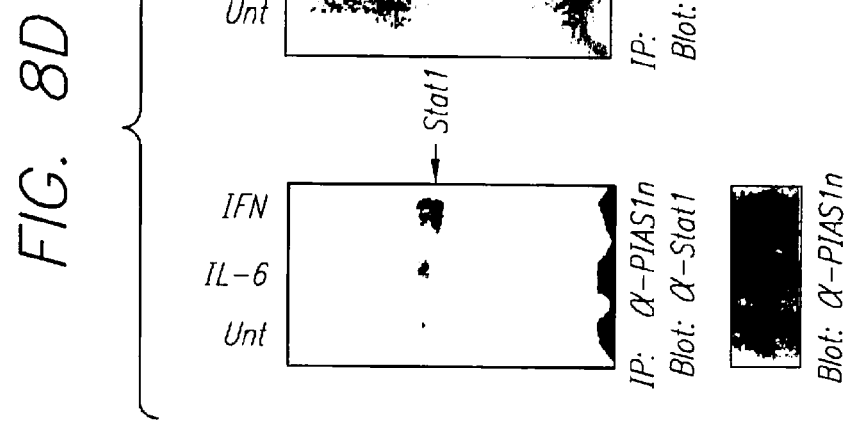
Figure 8C:
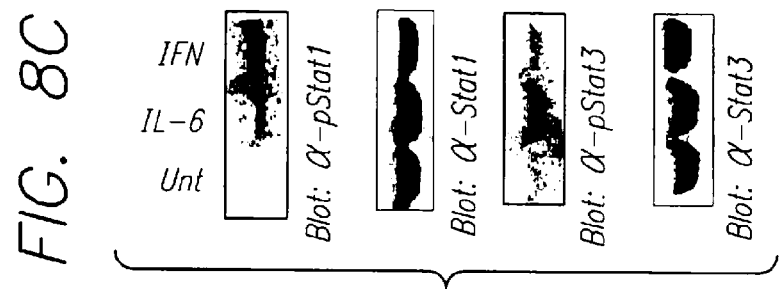

In panel B of FIG. 8 PIAS1 does not interact with STAT2. Daudi cells were treated with IFN-γ for the times indicated. Whole cell extracts were prepared and one half of these extracts were used for immunoprecipitation with anti-PIAS1n (left panel). Immunoprecipitation was carried out as described in (A) and the filter was probed with anti-STAT1 and anti-STAT2. The same filter was washed and reprobed with anti-PIAS1n (lower panel). The other half of protein extracts were subjected to immunoprecipitation with anti-STAT1 (right panel). The filter was probed with a mixture of anti-STAT1 and anti-STAT2 antibodies. p-STAT1: phosphorylated STAT1.

Human Daudi B cells were untreated or treated with IFN-α for various time periods. Protein extracts were prepared and subjected to immunoprecipitation with anti-PIAS1n followed by immunoblot with both anti-STAT1 and STAT2 antibodies. While STAT1 was associated with PIAS1 in IFN-treated cells, STAT2 was absent in PIAS1 immunoprecipitates (FIG. 8B).

In contrast, STAT2 was found to be present in STAT1 immunoprecipitates (FIG. 8B). This is consistent with the fact that upon IFN-α stimulation, a fraction of STAT1 and STAT2 proteins can form heterodimers (Kim et al. (1996)). These results further suggest that PIAS1 specifically interacts with STAT1 but not STAT2.

Panel C of FIG. 8 provides a Western blot analysis. HepG2 cells were untreated or treated with IL6 or IFN-γ for 15 min and protein extracts were prepared and analyzed by immunoblot with anti-STAT1, or anti-pSTAT1 (NEB), or anti-STAT3 (Santa Cruz, Calif.), or anti-pSTAT3 (NEB) as indicated.

In panel D of FIG. 8 PIAS1 interacts with STAT1 but not STAT3. Protein extracts from (C) were immunoprecipitated with anti-PIAS1n. The precipitates were subjected to electrophoresis and the filter was blotted with anti-STAT1 (left panel). The same filter was washed and reprobed with anti-STAT3 (left panel) or reprobed with anti-PIAS1n (lower panel). (E) Same as (D) except that anti-PIAS3c was used for immunoprecipitation. The filter was probed with anti-STAT3 (left panel) or anti-STAT1 (right panel) or PIAS3c (lower panel). Immunoprecipitation analysis was performed as described (Durbin et al. (1996)).

PIAS3 is a specific inhibitor of STAT3 signaling (Durbin et al. (1996)). To examine the specificity of PIAS-STAT interactions, in vivo co-immunoprecipitation analysis was carried out with protein extracts prepared from human HepG2 cells untreated or treated with IFN-γ or IL6.

IFN-γ treatment activates STAT1, but not STAT3, in HepG2 cells—as shown by immunoblot analysis with antisera that can specifically recognize tyrosine phosphorylated STAT1 or STAT3 (FIG. 8D). IL6 treatment strongly induces the tyrosine phosphorylation of STAT3 but only weekly stimulates phosphorylation of STAT1 in HepG2 cells. Samples of the same protein extracts were subjected to immunoprecipitation analysis with anti-PIAS1n or anti-PIAS3c [an antiserum against the COOH-terminal 79 amino acid residues of PIAS3 (Durbin et al. (1996))]. The immunoprecipitates were then analyzed by protein blot with anti-STAT1 or anti-STAT3.

PIAS1 was found to be associated with STAT1 but not STAT3 (FIG. 8D). Since the activation of STAT1 by IL6 was weak, the association of PIAS1 with STAT1 in IL6 treated HepG2 cells was observed only when the blot was overexposed. In contrast, PIAS3 was found to be associated with STAT3, but not STAT1 (FIG. 8E). These experiments further suggest that individual PIAS molecules display specificity for STATs in vivo.

Upon IFN stimulation, STAT1 becomes tyrosine phosphorylated on a single tyrosine residue Tyr-701. This phosphorylation is required for the dimerization, nuclear translocation and DNA binding activity of STAT1 (Shuai et al. Science (1993); Shuai et al. Cell (1994)). Since PIAS1 is associated with STAT1 only in ligand-stimulated cells, it was determined whether IFN-induced tyrosine phosphorylation of STAT1 is required for the in vivo PIAS1-STAT1 interaction.

Two stable cell lines, Ctyr and C91, derived from U3A cells which do not express STAT1 protein (Muller et al. (1993)) were used for co-immunoprecipitation analysis. C91 and Ctyr cell lines were established by complementing U3A cells with the wild type STAT1 and a mutant STAT1 (Tyr-701→Phe), respectively (Shuai et al. Science (1993)). Phosphotyrosine blot analysis confirmed that the T701F STAT1 mutant protein was not tyrosine phosphorylated in respond to IFN-γ stimulation (FIG. 9A).

FIG. 9 shows that phosphorylation on Tyr-701 of STAT1 is required for PIAS1-STAT1 interaction. U3A cells complemented with STAT1 or STAT1(Tyr-701→Phe) mutant protein were established as described (Darnell et al. (1994)). Cells were untreated or treated with IFN-γ for 15 minutes and protein extracts were prepared. In panel A of FIG. 9 immunoprecipitation was performed with anti-STAT1 followed by blotting with a specific phosphotyrosine antiserum [anti-pTyr (Transduction Laboratories, Lexington, Ky.)]. The same filter was washed and reprobed with anti-STAT1 (lower panel).

In panel B of FIG. 9 immunoprecipitation was performed with anti-PIAS1n antiserum and blotted with anti-STAT1. The filter was washed and reprobed with anti-PIAS1 (lower panel). U3A and U3A-derived cell lines were maintained in Dulbecco's modified Eagle's medium containing 10% fetal bovine serum at 10% $CO_2$.

STAT1 was clearly co-immunoprecipitated by anti-PIAS1 from C91 cells treated with IFN-γ (FIG. 9B). In contrast, anti-PIAS1 antibody failed to co-immunoprecipitate the T701P STAT1 mutant protein from Ctyr cells. These results suggest that IFN-induced phosphorylation on Tyr-701 of STAT1 is required for PIAS1-STAT1 interaction.

The identification of a family of PIAS molecules and the striking specific in vivo association between individual PIAS and STAT proteins strongly suggest the possible involvement of a specific PIAS inhibitor in every STAT signaling pathway. While not wishing to be bound by any specific theory, since PIAS molecules do not contain phosphotyrosine binding domains such as SH2 or PTB (Cohen et al. (1995); Pawson et al. (1997)), it seems likely that tyrosine phosphorylation of STATs may induce a protein conformational change, resulting the exposure of the PIAS binding domain.

PIAS molecules contain a conserved putative zinc binding motif which is present in many proteins including transcription factors. Interestingly, a N-terminal truncated mutant PIASxB protein (from amino acid 134 to 621), Mizl, was recently shown to interact with a homeobox DNA binding protein Msx2 (Wu et al. (1997)). In addition, Mizl was shown to have sequence specific DNA binding activity (Wu et al. (1997)). Thus, a PIAS molecule may play a dual functional role of inhibiting the expression of genes containing STAT binding sites while activating another distinct set of genes.

In summary, a family of PIAS (protein inhibitor of activated STAT) proteins were isolated. PIAS1, but not other PIAS molecules, blocked the DNA binding activity of STAT1 and inhibited STAT1-mediated gene activation in response to interferon (IFN). Co-immunoprecipitation analysis showed that PIAS1 was associated with STAT1 but not STAT2 or STAT3 following ligand stimulation. The in vivo PIAS1-STAT1 interaction requires phosphorylation of STAT1 on Tyr-701. These results demonstrated the specificity of PIAS-STAT interaction and suggest that there may exist a specific PIAS inhibitor in every STAT signaling pathway.

REFERENCES

Z. Zhong, Z. Wen, J. E. Darnell Jr., Science 264, 95 (1994); Proc. Nat. Acad. Sci. U.S.A. 91, 4806 (1995).
S. Akira et al., Cell 77, 63 (1994).
Y. Zhang et al., Nature 372, 425 (1994).
C. Vaisse et al., Nature Gen. 14, 95 (1996).
K. Takeda et al., Proc. Natl. Acad. Sci. USA. 94, 3801 (1997).
J. E. Darnell Jr., I. M. Kerr, G. M. Stark, Science 264, 1415 (1994)
C. Schindler and J. E. Darnell Jr., Annu. Rev. Biochem. 64, 621 (1995)
J. N. Ihie, Nature 377, 591 (1995); J. J. O'Shea, Immunity 7, 1 (1997)
H. B. Sadowski, K. Shuai, J. E. Darnell Jr., M. Z. Gilman, Science 261, 1739 (1993).
Z. Wen, Z. Zhong, J. E. Darnell Jr., Cell 82, 241 (1995).
T. Naka et al., Nature 387, 924 (1997).
T. A. Endo et al, (1997) Nature 387:921-924.
R. Starr et al., (1997) Nature 387:917-921.
K. Shuai, C. Schindler, V. R Prezioso, J. E. Darnell Jr., Science 258, 1808 (1992).
T. Leveillard and I. M. Verma, Gene Expr. 3, 135 (1993).
C. A. Chen and H. Okayama, Biotechniques 6, 632 (1988).
K. Shuai, G. R. Stark, I. M. Kerr, J. E. Darnell Jr., Science 261, 1744 (1993).
J. E. Darnell, Jr., I. M. Kerr, G. M. Stark, Science 264, 1415 (1994).
J. N. Ihle, Nature 377, 591 (1995).

T. Taniguchi, *Science* 268, 251 (1995).
J. E. Jr. Darnell, *Science* 277, 1630 (1997).
J. J. O'Shea, *Immunity* 7, 1 (1997).
M. A. Meraz et al., *Cell* 84, 431 (1996).
J. E. Durbin, R. Hackenmiller, M. C. Simon, D. E. Levy, (1996) *Cell* 84:443-450.
Shuai, K. et al. (1993) Nature 366:580-583.
J. Gyuris, E. Golemis, H. Chertkov, R. Brent, *Cell* 75, 791 (1993).
C. Schindler, X.-Y. Fu, T. Improta, R. Aebersold, J. E. Darnell, Jr., *Proc. Natl. Acad. Sci. USA* 89, 7836 (1992).
C. D. Chung, J. Liao, B. Liu, X. Rao, P. Jay, et al, *Science* 278, 1803 (1997).
B. C. Valdez, D. Henning, L. Perlaky, R. K. Busch, H. Busch, *Biochem. Biophys. Res. Commun.* 234, 335 (1997).
K. D. Kahn et al., *Proc. Natl. Acad. Sci. USA* 90, 6806 (1993)
Z. Wen, Z. Zhong, J. E. Darnell, Jr., *Cell* 82, 241 (1995).
C. Schindler, K. Shuai, V. R. Prezioso, J. E. Darnell, Jr., *Science* 257, 809 (1992).
X.-Y. Fu, *Cell* 70, 323 (1992).
T. Improta, C. Schindler, C. M. Horvath, I. M. Kerr, G. R. Stark, et al, *Proc. Natl. Acad. Sci. USA* 91, 4776 (1994).
K. Shuai, C. M. Horvath, L. H. Tsai-Huang, S. Qureshi, D. Cowburn, et al, *Cell* 76, 821 (1994)
K. Shuai, G. R. Stark, I. M. Kerr, J. E. Darnell, Jr., *Science* 261, 1744 (1993).
M. Muller et al., *EMBO J.* 12, 4221 (1993).
G. B. Cohen, R. Ren, D. Baltimore, *Cell* 80, 237 (1995); T. Pawson, J. D. Scott, *Science* 278, 2075 (1997).
L. Wu, H. Wu, F. Sangiorgi, N. Wu, J. R. Bell, et al, *Mech. of Devel.* 65, 3 (1997).
H. B. Sadowski, K Shuai, J. E. Darnell, Jr., M. Z. Gilman, *Science* 261, 1739 (1993).

---

What is claimed is:

1. A purified protein inhibitor of activated STAT (PIAS) molecule comprising the amino acid sequence selected from the group consisting of SEQ ID NO:1, residues 1-425 of SEQ ID NO:2, SEQ ID NO:3, SEQ ID NO:4, SEQ ID NO:5, SEQ ID NO:6, SEQ ID NO:7, SEQ ID NO:9, SEQ ID NO:10 and SEQ ID NO:12, wherein said PIAS molecule specifically recognizes and binds a signal transducer and activator of transcription (STAT) protein thereby inhibiting the activity of said STAT protein, wherein the STAT protein is STAT1 or STAT3.

2. The PIAS molecule of claim 1 which binds STAT3 but not STAT1.

3. The PIAS molecule of claim 2 designated murine PIAS3 and having the sequence shown in SEQ ID NO: 1.

4. The PIAS molecule of claim 2 designated human PIAS3 and having the sequence shown in SEQ ID NO: 9.

5. The PIAS molecule of claim 2, wherein the STAT3 is a homodimer.

6. The PIAS molecule of claim 2, wherein the STAT3 is a heterodimer.

7. The PIAS molecule of claim 2, wherein the STAT3 is STAT3($\alpha$).

8. The PIAS molecule of claim 2, wherein the STAT3 is STAT3-$\beta$.

9. The PIAS molecule of claim 1 which binds STAT1 but does not bind STAT3.

10. The PIAS molecule of claim 9 designated human PIAS1 and having the sequence shown in SEQ ID NO: 2.

11. The PIAS molecule of claim 9 designated murine PIAS1 and having the sequence shown in SEQ ID NO: 3.

12. The PIAS molecule of claim 1 designated human PIASx$\alpha$ and having the sequence shown in SEQ ID NO: 5.

13. The PIAS molecule of claim 1 designated human PIASx$\beta$ and having the sequence shown in SEQ ID NO: 6.

14. The PIAS molecule of claim 1 designated human PIASy and having the sequence shown in SEQ ID NO: 7.

15. The PIAS molecule of claim 9, wherein the STAT1 is a homodimer.

16. The PIAS molecule of claim 9, wherein the STAT1 is a heterodimer.

17. The PIAS molecule of claim 9, wherein the STAT1 is STAT1($\alpha$).

18. The PIAS molecule of claim 9, wherein the is STAT1 is STAT1-$\beta$.

19. A method for blocking the DNA-binding activity of a STAT protein comprising contacting the PIAS molecule of claim 1 with STAT so as to block the DNA-binding activity of the STAT protein.

20. The method of claim 19, wherein the PIAS molecule is PIAS1.

21. The method of claim 19, wherein the PIAS molecule is PIAS3.

22. The method of claim 19, wherein the PIAS molecule is PIASx$\alpha$.

23. The method of claim 19, wherein the PIAS molecule is PIASx$\beta$.

24. The method of claim 19, wherein the PIAS molecule is PIASy.

25. The method of claim 19, wherein the STAT protein is STAT1.

26. The method of claim 19, wherein the STAT protein is STAT3.

* * * * *

UNITED STATES PATENT AND TRADEMARK OFFICE
CERTIFICATE OF CORRECTION

| | | |
|---|---|---|
| PATENT NO. | : 7,265,202 B1 | Page 1 of 1 |
| APPLICATION NO. | : 09/573651 | |
| DATED | : September 4, 2007 | |
| INVENTOR(S) | : Shuai et al. | |

It is certified that error appears in the above-identified patent and that said Letters Patent is hereby corrected as shown below:

In the specification, Column 1, Line 20, insert the following paragraph:

--GOVERNMENT RIGHTS

This invention was made with government support under grant number AI39612 awarded by the National Institutes of Health. The government has certain rights in the invention.--

Signed and Sealed this

Thirteenth Day of May, 2008

JON W. DUDAS
*Director of the United States Patent and Trademark Office*

SEQUENCE LISTING

```
<160> NUMBER OF SEQ ID NOS: 13

<210> SEQ ID NO 1
<211> LENGTH: 583
<212> TYPE: PRT
<213> ORGANISM: Mouse

<400> SEQUENCE: 1

Met Val Met Ser Phe Arg Val Ser Glu Leu Gln Val Leu Leu Gly Phe
1               5                   10                  15

Ala Gly Arg Asn Lys Ser Gly Arg Lys His Glu Leu Leu Ala Lys Ala
            20                  25                  30

Leu His Leu Leu Lys Ser Ser Cys Ala Pro Ser Val Gln Met Lys Ile
        35                  40                  45

Lys Glu Leu Tyr Arg Arg Arg Phe Pro Arg Lys Thr Leu Gly Pro Ser
    50                  55                  60

Asp Leu Ser Leu Leu Ser Leu Pro Pro Gly Thr Ser Pro Pro Val His
65                  70                  75                  80

Pro Asp Val Thr Met Lys Pro Leu Pro Phe Tyr Glu Val Tyr Gly Glu
                85                  90                  95

Leu Ile Arg Pro Thr Thr Leu Ala Ser Thr Ser Ser Gln Arg Phe Glu
            100                 105                 110

Glu Ala His Phe Thr Phe Ala Leu Thr Pro Gln Gln Leu Gln Gln Ile
        115                 120                 125

Leu Thr Ser Arg Glu Val Leu Pro Gly Ala Lys Cys Asp Tyr Thr Ile
    130                 135                 140

Gln Val Gln Leu Arg Phe Cys Leu Cys Glu Thr Ser Cys Pro Gln Glu
145                 150                 155                 160

Asp Tyr Phe Pro Pro Asn Leu Phe Val Lys Val Asn Gly Lys Leu Cys
                165                 170                 175

Pro Leu Pro Gly Tyr Leu Pro Pro Thr Lys Asn Gly Ala Glu Pro Arg
            180                 185                 190

Gly Pro Ala Val Arg Ser Thr Ser His Pro Trp Leu Asp Ser Gln Pro
        195                 200                 205

Leu Ser Pro Thr Pro Ser Leu Leu Ile Gly His Leu Ser Leu Asp Gly
    210                 215                 220

Ile Thr Pro Cys Pro Cys Leu Val Arg Gln Leu Thr Ala Gly Thr Leu
```

-continued

```
            225                 230                 235                 240

Leu Gln Lys Leu Arg Ala Lys Gly Ile Arg Asn Pro Asp His Ser Arg
                245                 250                 255

Ala Leu Ile Lys Glu Lys Leu Thr Ala Asp Pro Asp Ser Glu Val Ala
                260                 265                 270

Thr Thr Ser Leu Pro Gly Val Thr His Val Pro Ala Arg Lys Met Arg
            275                 280                 285

Leu Thr Val Pro Cys Arg Ala Leu Thr Cys Ala His Leu Gln Ser Phe
            290                 295                 300

Asp Ala Ala Leu Tyr Leu Gln Met Asn Glu Lys Lys Pro Thr Trp Thr
305                 310                 315                 320

Cys Pro Val Cys Asp Lys Lys Ala Pro Tyr Glu Ser Leu Ile Ile Asp
                325                 330                 335

Gly Leu Phe Met Glu Ile Leu Asn Ser Cys Ser Asp Asp Glu Ile
                340                 345                 350

Gln Phe Met Glu Asp Gly Ser Trp Cys Pro Met Lys Pro Lys Lys Glu
            355                 360                 365

Ala Ser Glu Val Cys Pro Pro Gly Tyr Gly Leu Asp Gly Leu Gln
            370                 375                 380

Tyr Ser Ala Val Gln Glu Gly Ile Gln Pro Glu Ser Lys Lys Arg Val
385                 390                 395                 400

Glu Val Ile Asp Leu Thr Ile Glu Ser Ser Ser Asp Glu Glu Asp Leu
                405                 410                 415

Pro Pro Thr Lys Lys His Cys Ser Pro Thr Ser Ala Ala Ile Pro Ala
                420                 425                 430

Leu Pro Gly Ser Lys Gly Ala Leu Thr Ser Gly His Gln Pro Ser Ser
            435                 440                 445

Val Leu Arg Ser Pro Ala Met Gly Thr Leu Gly Ser Asp Phe Leu Ser
            450                 455                 460

Ser Leu Pro Val His Glu Tyr Pro Pro Ala Phe Pro Leu Gly Ala Asp
465                 470                 475                 480

Ile Gln Gly Leu Asp Leu Phe Ser Phe Leu Gln Thr Glu Ser Gln Gln
                485                 490                 495

Tyr Gly Pro Ser Val Ile Ser Leu Asp Glu Gln Asp Thr Leu Gly
            500                 505                 510

His Phe Phe Gln Tyr Arg Gly Thr Pro Ser His Phe Leu Gly Pro Leu
            515                 520                 525

Ala Pro Thr Leu Gly Ser Cys His Gly Ser Ser Thr Pro Ala Pro Pro
            530                 535                 540

Pro Gly Arg Val Ser Ser Ile Val Ala Pro Gly Ser Ser Leu Arg Glu
545                 550                 555                 560

Gly His Gly Gly Pro Leu Pro Ser Gly Pro Ser Leu Thr Gly Cys Arg
                565                 570                 575

Ser Asp Val Ile Ser Leu Asp
            580

<210> SEQ ID NO 2
<211> LENGTH: 650
<212> TYPE: PRT
<213> ORGANISM: Human

<400> SEQUENCE: 2

Met Ala Asp Ser Ala Glu Leu Lys Gln Met Val Met Ser Leu Arg Val
1               5                   10                  15
```

-continued

```
Ser Glu Leu Gln Val Leu Leu Gly Tyr Ala Gly Arg Asn Lys His Gly
             20                  25                  30

Arg Lys His Glu Leu Leu Thr Lys Ala Leu His Leu Leu Lys Ala Gly
         35                  40                  45

Cys Ser Pro Ala Val Gln Met Lys Ile Lys Glu Leu Tyr Arg Arg Arg
 50                  55                  60

Phe Pro Gln Lys Ile Met Thr Pro Ala Asp Leu Ser Ile Pro Asn Val
 65                  70                  75                  80

His Ser Ser Pro Met Pro Ala Thr Leu Ser Pro Ser Thr Ile Pro Gln
                 85                  90                  95

Leu Thr Tyr Asp Gly His Pro Ala Ser Ser Pro Leu Leu Pro Val Ser
            100                 105                 110

Leu Leu Gly Pro Lys His Lys Leu Glu Leu Pro His Leu Thr Ser Ala
        115                 120                 125

Leu His Pro Val His Pro Asp Ile Lys Leu Gln Lys Leu Pro Phe Tyr
    130                 135                 140

Asp Leu Leu Asp Glu Leu Ile Lys Pro Thr Ser Leu Ala Ser Asp Asn
145                 150                 155                 160

Ser Gln Arg Phe Arg Glu Thr Cys Phe Ala Phe Ala Leu Thr Pro Gln
                165                 170                 175

Gln Val Gln Gln Ile Ser Ser Ser Met Asp Ile Ser Gly Thr Lys Cys
            180                 185                 190

Asp Phe Thr Val Gln Val Gln Leu Arg Phe Cys Leu Ser Glu Thr Ser
        195                 200                 205

Cys Pro Gln Glu Asp His Phe Pro Pro Asn Leu Cys Val Lys Val Asn
    210                 215                 220

Thr Lys Pro Cys Ser Leu Pro Gly Tyr Leu Pro Pro Thr Lys Asn Gly
225                 230                 235                 240

Val Glu Pro Lys Arg Pro Ser Arg Pro Ile Asn Ile Thr Ser Leu Val
                245                 250                 255

Arg Leu Ser Thr Thr Val Pro Asn Thr Met Cys Ser Trp Thr Ala Glu
            260                 265                 270

Ile Gly Arg Asn Tyr Ser Met Ala Val Tyr Leu Val Lys Gln Leu Ser
        275                 280                 285

Ser Thr Val Leu Leu Gln Arg Leu Arg Ala Lys Gly Ile Arg Asn Pro
    290                 295                 300

Asp His Ser Arg Ala Leu Ile Lys Glu Lys Leu Thr Ala Asp Pro Asp
305                 310                 315                 320

Ser Glu Ile Ala Thr Thr Ser Leu Arg Val Ser Leu Leu Cys Pro Leu
                325                 330                 335

Gly Lys Met Arg Leu Thr Ile Pro Cys Arg Ala Leu Thr Cys Ser His
            340                 345                 350

Leu Gln Cys Phe Asp Ala Thr Leu Tyr Ile Gln Met Asn Glu Lys Lys
        355                 360                 365

Pro Thr Trp Val Cys Pro Val Cys Asp Lys Lys Ala Pro Tyr Glu His
    370                 375                 380

Leu Ile Ile Asp Gly Leu Phe Met Glu Ile Leu Lys Tyr Cys Thr Asp
385                 390                 395                 400

Cys Asp Glu Ile Gln Phe Lys Glu Asp Gly Thr Trp Ala Pro Met Arg
                405                 410                 415

Ser Lys Lys Glu Val Gln Glu Val Ser Ala Ser Tyr Asn Gly Val Asp
            420                 425                 430

Gly Cys Leu Ser Ser Thr Leu Glu His Gln Val Ala Ser His His Gln
```

```
                435                 440                 445
Ser Ser Asn Lys Asn Lys Val Glu Val Ile Asp Leu Thr Ile Asp
    450                 455                 460
Ser Ser Ser Asp Glu Glu Glu Pro Ser Ala Lys Arg Thr Cys
465                 470                 475                 480
Pro Ser Leu Ser Pro Thr Ser Pro Leu Asn Asn Lys Gly Ile Leu Ser
                485                 490                 495
Leu Pro His Gln Ala Ser Pro Val Ser Arg Thr Pro Ser Leu Pro Ala
            500                 505                 510
Val Asp Thr Ser Tyr Ile Asn Thr Ser Leu Ile Gln Asp Tyr Arg His
            515                 520                 525
Pro Phe His Met Thr Pro Met Pro Tyr Asp Leu Gln Gly Leu Asp Phe
    530                 535                 540
Phe Pro Phe Leu Ser Gly Asp Asn Gln His Tyr Asn Thr Ser Leu Leu
545                 550                 555                 560
Ala Ala Ala Ala Ala Val Ser Asp Asp Gln Asp Leu Leu His Ser
                565                 570                 575
Ser Arg Phe Phe Pro Tyr Thr Ser Ser Gln Met Phe Leu Asp Gln Leu
            580                 585                 590
Ser Ala Gly Gly Ser Thr Ser Leu Pro Thr Thr Asn Gly Ser Ser Ser
            595                 600                 605
Gly Ser Asn Ser Ser Leu Val Ser Ser Asn Ser Leu Arg Glu Ser His
        610                 615                 620
Ser His Thr Val Thr Asn Arg Ser Ser Thr Asp Thr Ala Ser Ile Phe
625                 630                 635                 640
Gly Ile Ile Pro Asp Ile Ile Ser Leu Asp
                645                 650

<210> SEQ ID NO 3
<211> LENGTH: 650
<212> TYPE: PRT
<213> ORGANISM: Mouse

<400> SEQUENCE: 3

Met Ala Asp Ser Ala Glu Leu Lys Gln Met Val Met Ser Leu Arg Val
1               5                   10                  15
Ser Glu Leu Gln Val Leu Leu Gly Tyr Ala Gly Arg Asn Lys His Gly
                20                  25                  30
Arg Lys His Glu Leu Leu Thr Lys Ala Leu His Leu Leu Lys Ala Gly
            35                  40                  45
Cys Ser Pro Ala Val Gln Met Lys Ile Lys Glu Leu Tyr Arg Arg Arg
    50                  55                  60
Phe Pro Gln Lys Ile Met Thr Pro Ala Asp Leu Ser Ile Pro Asn Val
65                  70                  75                  80
His Ser Ser Pro Met Pro Pro Thr Leu Ser Pro Ser Thr Ile Pro Gln
                85                  90                  95
Leu Thr Tyr Asp Gly His Pro Ala Ser Ser Pro Leu Leu Pro Val Ser
            100                 105                 110
Leu Leu Gly Pro Lys His Glu Leu Glu Leu Pro His Leu Thr Ser Ala
        115                 120                 125
Leu His Pro Val His Pro Asp Ile Lys Leu Gln Lys Leu Pro Phe Tyr
    130                 135                 140
Asp Leu Leu Asp Glu Leu Ile Lys Pro Thr Ser Leu Ala Ser Asp Asn
145                 150                 155                 160
```

```
Ser Gln Arg Phe Arg Glu Thr Cys Phe Ala Phe Ala Leu Thr Pro Gln
            165                 170                 175
Gln Val Gln Gln Ile Ser Ser Met Asp Ile Ser Gly Thr Lys Cys
                180                 185                 190
Asp Phe Thr Val Gln Val Gln Leu Arg Phe Cys Leu Ser Glu Thr Ser
        195                 200                 205
Cys Pro Gln Glu Asp His Phe Pro Pro Asn Leu Cys Val Lys Val Asn
    210                 215                 220
Thr Lys Pro Cys Ser Leu Pro Gly Tyr Leu Pro Pro Thr Lys Asn Gly
225                 230                 235                 240
Val Glu Pro Lys Arg Pro Ser Arg Pro Ile Asn Ile Thr Ser Leu Val
                245                 250                 255
Arg Leu Ser Thr Thr Val Pro Asn Thr Ile Val Val Ser Trp Thr Ala
                260                 265                 270
Glu Ile Gly Arg Asn Tyr Ser Met Ala Val Tyr Leu Val Lys Gln Leu
                275                 280                 285
Ser Ser Thr Val Leu Leu Gln Arg Leu Arg Ala Lys Gly Ile Arg Asn
    290                 295                 300
Pro Asp His Ser Arg Ala Leu Ile Lys Glu Lys Leu Thr Ala Asp Ser
305                 310                 315                 320
Asp Ser Glu Ile Ala Thr Thr Ser Leu Arg Val Ser Leu Leu Cys Pro
                325                 330                 335
Leu Gly Lys Met Arg Leu Thr Ile Pro Cys Arg Ala Leu Thr Cys Ser
                340                 345                 350
His Leu Gln Cys Phe Asp Ala Thr Leu Tyr Ile Gln Met Asn Glu Lys
            355                 360                 365
Lys Pro Thr Trp Val Cys Pro Val Cys Asp Lys Lys Ala Pro Tyr Glu
            370                 375                 380
His Leu Ile Ile Asp Gly Leu Phe Met Glu Ile Leu Lys Tyr Cys Thr
385                 390                 395                 400
Asp Cys Asp Glu Ile Gln Phe Lys Glu Asp Gly Ser Trp Ala Pro Met
                405                 410                 415
Arg Ser Lys Lys Val Gln Glu Val Thr Ala Ser Tyr Asn Gly Val Asp
            420                 425                 430
Gly Cys Leu Ser Ser Thr Leu Glu His Gln Val Ala Ser His Asn Gln
            435                 440                 445
Ser Ser Asn Lys Asn Lys Lys Val Glu Val Ile Asp Leu Thr Ile Asp
    450                 455                 460
Ser Ser Ser Asp Glu Glu Glu Glu Pro Pro Ala Lys Arg Thr Cys
465                 470                 475                 480
Pro Ser Leu Ser Pro Thr Ser Pro Leu Ser Asn Lys Gly Ile Leu Ser
            485                 490                 495
Leu Pro His Gln Ala Ser Pro Val Ser Arg Thr Pro Ser Leu Pro Ala
                500                 505                 510
Val Asp Thr Ser Tyr Ile Asn Thr Ser Leu Ile Gln Asp Tyr Arg His
            515                 520                 525
Pro Phe His Met Thr Pro Met Pro Tyr Asp Leu Gln Gly Leu Asp Phe
            530                 535                 540
Phe Pro Phe Leu Ser Gly Asp Asn Gln His Tyr Asn Thr Ser Leu Leu
545                 550                 555                 560
Ala Ala Ala Ala Ala Ala Val Ser Asp Asp Gln Asp Leu Leu His Ser
                565                 570                 575
Ser Arg Phe Phe Pro Tyr Thr Ser Ser Gln Met Phe Leu Asp Gln Leu
```

```
                   580                 585                 590
Ser Ala Gly Gly Ser Thr Ser Leu Pro Ala Thr Asn Gly Ser Ser Ser
            595                 600                 605

Gly Ser Asn Ser Ser Leu Val Ser Ser Asn Ser Leu Arg Glu Ser His
        610                 615                 620

Gly His Gly Val Ala Ser Arg Ser Ser Ala Asp Thr Ala Ser Ile Phe
625                 630                 635                 640

Gly Ile Ile Pro Asp Ile Ile Ser Leu Asp
                645                 650

<210> SEQ ID NO 4
<211> LENGTH: 584
<212> TYPE: PRT
<213> ORGANISM: Mouse

<400> SEQUENCE: 4

Met Val Met Ser Phe Arg Val Ser Glu Leu Gln Val Leu Leu Gly Phe
1               5                   10                  15

Ala Gly Arg Asn Lys Ser Gly Arg Lys His Glu Leu Leu Ala Lys Ala
            20                  25                  30

Leu His Leu Leu Lys Ser Ser Cys Ala Pro Ser Val Gln Met Lys Ile
        35                  40                  45

Lys Glu Leu Tyr Arg Arg Arg Phe Pro Arg Lys Thr Leu Gly Pro Ser
    50                  55                  60

Asp Leu Ser Leu Leu Ser Leu Pro Pro Gly Thr Ser Pro Val His
65                  70                  75                  80

Pro Asp Val Thr Met Lys Pro Leu Pro Phe Tyr Glu Val Tyr Gly Glu
                85                  90                  95

Leu Ile Arg Pro Thr Thr Leu Ala Ser Thr Ser Ser Gln Arg Phe Glu
            100                 105                 110

Glu Ala His Phe Thr Phe Ala Leu Thr Pro Gln Gln Leu Gln Gln Ile
        115                 120                 125

Leu Thr Ser Arg Glu Val Leu Pro Gly Ala Lys Cys Asp Tyr Thr Ile
    130                 135                 140

Gln Val Gln Leu Arg Phe Cys Leu Cys Glu Thr Ser Cys Pro Gln Glu
145                 150                 155                 160

Asp Tyr Phe Pro Pro Asn Leu Phe Val Lys Val Asn Gly Lys Leu Cys
                165                 170                 175

Pro Leu Pro Gly Tyr Leu Pro Pro Thr Lys Asn Gly Ala Glu Pro Arg
            180                 185                 190

Gly Pro Ala Val Arg Ser Thr Ser His Pro Trp Leu Asp Ser Gln Pro
        195                 200                 205

Leu Ser Pro Thr Pro Ser Leu Leu Ile Gly His Leu Ser Leu Asp Gly
    210                 215                 220

Ile Thr Pro Cys Pro Cys Leu Val Arg Gln Leu Thr Ala Gly Thr Leu
225                 230                 235                 240

Leu Gln Lys Leu Arg Ala Lys Gly Ile Arg Asn Pro Asp His Ser Arg
                245                 250                 255

Ala Leu Ile Lys Glu Lys Leu Thr Ala Asp Pro Asp Ser Glu Val Ala
            260                 265                 270

Thr Thr Ser Leu Pro Gly Val Thr His Val Pro Ala Arg Lys Met Arg
        275                 280                 285

Leu Thr Val Pro Cys Arg Ala Leu Thr Cys Ala His Leu Gln Ser Phe
    290                 295                 300
```

-continued

```
Asp Ala Ala Leu Tyr Ile Gln Met Asn Glu Lys Lys Pro Thr Trp Thr
305                 310                 315                 320

Cys Pro Val Cys Asp Lys Lys Ala Pro Tyr Glu Ser Leu Ile Ile Asp
                325                 330                 335

Gly Leu Phe Met Glu Ile Leu Asn Ser Cys Ser Asp Cys Asp Glu Ile
            340                 345                 350

Gln Phe Met Glu Asp Gly Ser Trp Cys Pro Met Lys Pro Lys Lys Glu
        355                 360                 365

Ala Ser Glu Val Cys Pro Pro Gly Tyr Gly Leu Asp Gly Leu Gln
    370                 375                 380

Tyr Ser Ala Val Gln Glu Gly Ile Gln Pro Glu Ser Lys Lys Arg Val
385                 390                 395                 400

Glu Val Ile Asp Leu Thr Ile Glu Ser Ser Asp Glu Glu Asp Leu
                405                 410                 415

Pro Pro Thr Lys Lys Gln Cys Ser Val Thr Ser Ala Ala Ile Pro Ala
                420                 425                 430

Leu Leu Gly Ser Lys Gly Val Leu Thr Ser Gly His Gln Pro Ser Ser
            435                 440                 445

Val Leu Arg Ser Pro Ala Met Gly Thr Leu Gly Ser Asp Phe Leu Ser
    450                 455                 460

Ser Leu Pro Val His Glu Tyr Pro Pro Ala Phe Pro Leu Gly Ala Asp
465                 470                 475                 480

Ile Gln Gly Leu Asp Leu Phe Ser Phe Leu Gln Thr Glu Ser Gln Gln
                485                 490                 495

Tyr Gly Pro Ser Val Ile Ile Ser Leu Asp Glu Gln Asp Thr Leu Gly
            500                 505                 510

His Phe Phe Gln Tyr Arg Gly Thr Pro Ser His Phe Leu Gly Pro Leu
        515                 520                 525

Ala Pro Thr Leu Gly Ser Cys His Gly Ser Ser Thr Pro Ala Pro Pro
    530                 535                 540

Pro Gly Arg Val Ser Ser Ile Val Ala Pro Gly Ser Ser Ser Leu Arg
545                 550                 555                 560

Glu Gly His Gly Gly Pro Leu Pro Ser Gly Pro Ser Leu Thr Gly Cys
                565                 570                 575

Arg Ser Asp Val Ile Ser Leu Asp
            580

<210> SEQ ID NO 5
<211> LENGTH: 572
<212> TYPE: PRT
<213> ORGANISM: Human

<400> SEQUENCE: 5

Met Ala Asp Phe Glu Glu Leu Arg Asn Met Val Ser Ser Phe Arg Val
1               5                   10                  15

Ser Glu Leu Gln Val Leu Leu Gly Phe Ala Gly Arg Asn Lys Ser Gly
            20                  25                  30

Arg Lys His Asp Leu Leu Met Arg Ala Leu His Leu Leu Lys Ala Ser
        35                  40                  45

Cys Ser Pro Ala Val Gln Ile Lys Ile Arg Glu Leu Tyr Arg Arg Arg
    50                  55                  60

Tyr Pro Arg Thr Leu Glu Gly Leu Ser Asp Leu Ser Thr Ile Lys Ser
65                  70                  75                  80

Ser Val Phe Ser Leu Asp Gly Gly Ser Ser Pro Val Glu Pro Asp Leu
                85                  90                  95
```

```
Ala Val Ala Gly Ile His Ser Leu Pro Ser Thr Ser Val Thr Pro His
            100                 105                 110

Ser Pro Ser Ser Pro Val Gly Ser Val Leu Leu Gln Asp Thr Lys Pro
        115                 120                 125

Thr Phe Glu Met Gln Gln Pro Ser Pro Pro Ile Pro Pro Val His Pro
    130                 135                 140

Asp Val Gln Leu Lys Asn Leu Pro Phe Tyr Asp Val Leu Asp Val Leu
145                 150                 155                 160

Ile Lys Pro Thr Ser Leu Val Gln Ser Ser Ile Gln Arg Phe Gln Glu
                165                 170                 175

Lys Phe Phe Ile Phe Ala Leu Thr Pro Gln Gln Val Arg Glu Ile Cys
            180                 185                 190

Ile Ser Arg Asp Phe Leu Pro Gly Gly Arg Arg Asp Tyr Thr Val Gln
        195                 200                 205

Val Gln Leu Arg Leu Cys Leu Ala Glu Thr Ser Cys Pro Gln Glu Asp
    210                 215                 220

Asn Tyr Pro Asn Ser Leu Cys Ile Lys Val Asn Gly Lys Leu Phe Pro
225                 230                 235                 240

Leu Pro Gly Tyr Ala Pro Pro Lys Asn Gly Ile Glu Gln Lys Arg
                245                 250                 255

Pro Gly Arg Pro Leu Asn Ile Thr Ser Leu Val Arg Leu Ser Ser Ala
            260                 265                 270

Val Pro Asn Gln Ile Ser Ile Ser Trp Ala Ser Glu Ile Gly Lys Asn
        275                 280                 285

Tyr Ser Met Ser Val Tyr Leu Val Arg Gln Leu Thr Ser Ala Met Leu
    290                 295                 300

Leu Gln Arg Leu Lys Met Lys Gly Ile Arg Asn Pro Asp His Ser Arg
305                 310                 315                 320

Ala Leu Ile Lys Glu Lys Leu Thr Ala Asp Pro Asp Ser Glu Ile Ala
                325                 330                 335

Thr Thr Ser Leu Arg Val Ser Leu Met Cys Pro Leu Gly Lys Met Arg
            340                 345                 350

Leu Thr Ile Pro Cys Arg Ala Val Thr Cys Thr His Leu Gln Cys Phe
        355                 360                 365

Asp Ala Ala Leu Tyr Ile Gln Met Asn Glu Lys Lys Pro Thr Trp Ile
    370                 375                 380

Cys Pro Val Cys Asp Lys Lys Ala Ala Tyr Glu Ser Leu Ile Leu Asp
385                 390                 395                 400

Gly Leu Phe Met Glu Ile Leu Asn Asp Cys Ser Asp Val Asp Glu Ile
                405                 410                 415

Lys Phe Gln Glu Asp Gly Ser Trp Cys Pro Met Arg Pro Lys Lys Glu
            420                 425                 430

Ala Met Lys Val Ser Ser Gln Pro Cys Thr Lys Ile Glu Ser Ser Ser
        435                 440                 445

Val Leu Ser Lys Pro Cys Ser Val Thr Val Ala Ser Glu Ala Ser Lys
    450                 455                 460

Lys Lys Val Asp Val Ile Asp Leu Thr Ile Glu Ser Ser Ser Asp Glu
465                 470                 475                 480

Glu Glu Asp Pro Pro Ala Lys Arg Lys Cys Ile Phe Met Ser Glu Thr
                485                 490                 495

Gln Ser Ser Pro Thr Lys Gly Val Leu Met Tyr Gln Pro Ser Ser Val
            500                 505                 510
```

```
Arg Val Pro Ser Val Thr Ser Val Asp Pro Ala Ala Ile Pro Pro Ser
        515                 520                 525

Leu Thr Asp Tyr Ser Val Pro Phe His His Thr Pro Ile Ser Ser Met
        530                 535                 540

Ser Ser Asp Leu Pro Gly Glu Gln Arg Asn Asp Ile Asn Asn Glu
545                 550                 555                 560

Leu Lys Leu Gly Thr Ser Ser Asp Thr Val Gln Gln
                565                 570

<210> SEQ ID NO 6
<211> LENGTH: 621
<212> TYPE: PRT
<213> ORGANISM: Human

<400> SEQUENCE: 6

Met Ala Asp Phe Glu Glu Leu Arg Asn Met Val Ser Ser Phe Arg Val
1               5                   10                  15

Ser Glu Leu Gln Val Leu Leu Gly Phe Ala Gly Arg Asn Lys Ser Gly
            20                  25                  30

Arg Lys His Asp Leu Leu Met Arg Ala Leu His Leu Leu Lys Ser Gly
        35                  40                  45

Cys Ser Pro Ala Val Gln Ile Lys Ile Arg Glu Leu Tyr Arg Arg Arg
    50                  55                  60

Tyr Pro Arg Thr Leu Glu Gly Leu Ser Asp Leu Ser Thr Ile Lys Ser
65                  70                  75                  80

Ser Val Phe Ser Leu Asp Gly Gly Ser Ser Pro Val Glu Pro Asp Leu
                85                  90                  95

Ala Val Ala Gly Ile His Ser Leu Pro Ser Thr Ser Val Thr Pro His
            100                 105                 110

Ser Pro Ser Ser Pro Val Gly Ser Val Leu Leu Gln Asp Thr Lys Pro
        115                 120                 125

Thr Phe Glu Met Gln Gln Pro Ser Pro Ile Pro Pro Val His Pro
    130                 135                 140

Asp Val Gln Leu Lys Asn Leu Pro Phe Tyr Asp Val Leu Asp Val Leu
145                 150                 155                 160

Ile Lys Pro Thr Ser Leu Val Gln Ser Ile Gln Arg Phe Gln Glu
                165                 170                 175

Lys Phe Phe Ile Phe Ala Leu Thr Pro Gln Gln Val Arg Glu Ile Cys
            180                 185                 190

Ile Ser Arg Asp Phe Leu Pro Gly Gly Arg Arg Asp Tyr Thr Val Gln
        195                 200                 205

Val Gln Leu Arg Leu Cys Leu Ala Glu Thr Ser Cys Pro Gln Glu Asp
    210                 215                 220

Asn Tyr Pro Asn Ser Leu Cys Ile Lys Val Asn Gly Lys Leu Phe Pro
225                 230                 235                 240

Leu Pro Gly Tyr Ala Pro Pro Pro Lys Asn Gly Ile Glu Gln Lys Arg
                245                 250                 255

Pro Gly Arg Pro Leu Asn Ile Thr Ser Leu Val Arg Leu Ser Ser Ala
            260                 265                 270

Val Pro Asn Gln Ile Ser Ile Ser Trp Ala Ser Glu Ile Gly Lys Asn
        275                 280                 285

Tyr Ser Met Ser Val Tyr Leu Val Arg Gln Leu Thr Ser Ala Met Leu
    290                 295                 300

Leu Gln Arg Leu Lys Met Lys Gly Ile Arg Asn Pro Asp His Ser Arg
305                 310                 315                 320
```

```
Ala Leu Ile Lys Glu Lys Leu Thr Ala Asp Pro Asp Ser Glu Ile Ala
            325                 330                 335

Thr Thr Ser Leu Arg Val Ser Leu Met Cys Pro Leu Gly Lys Met Arg
            340                 345                 350

Leu Thr Ile Pro Cys Arg Ala Val Thr Cys Thr His Leu Gln Cys Phe
            355                 360                 365

Asp Ala Ala Leu Tyr Ile Gln Met Asn Glu Lys Lys Pro Thr Trp Ile
            370                 375                 380

Cys Pro Val Cys Asp Lys Lys Ala Ala Tyr Glu Ser Leu Ile Leu Asp
385                 390                 395                 400

Gly Leu Phe Met Glu Ile Leu Asn Asp Cys Ser Asp Val Asp Glu Ile
            405                 410                 415

Lys Phe Gln Glu Asp Gly Ser Trp Cys Pro Met Arg Pro Lys Lys Glu
            420                 425                 430

Ala Met Lys Val Ser Ser Gln Pro Cys Thr Lys Ile Glu Ser Ser Ser
            435                 440                 445

Val Leu Ser Lys Pro Cys Ser Val Thr Val Ala Ser Glu Ala Ser Lys
            450                 455                 460

Lys Lys Val Asp Val Ile Asp Leu Thr Ile Glu Ser Ser Ser Asp Glu
465                 470                 475                 480

Glu Glu Asp Pro Pro Ala Lys Arg Lys Cys Ile Phe Met Ser Glu Thr
            485                 490                 495

Gln Ser Ser Pro Thr Lys Gly Val Leu Met Tyr Gln Pro Ser Ser Val
            500                 505                 510

Arg Val Pro Ser Val Thr Ser Val Asp Pro Ala Ala Ile Pro Pro Ser
            515                 520                 525

Leu Thr Asp Tyr Ser Val Pro Phe His His Thr Pro Ile Ser Ser Met
            530                 535                 540

Ser Ser Asp Leu Pro Gly Leu Asp Phe Leu Ser Leu Ile Pro Val Asp
545                 550                 555                 560

Pro Gln Tyr Cys Pro Pro Met Phe Leu Asp Ser Leu Thr Ser Pro Leu
            565                 570                 575

Thr Ala Ser Ser Thr Ser Val Thr Thr Thr Ser Ser His Glu Ser Ser
            580                 585                 590

Thr His Val Ser Ser Ser Ser Arg Ser Glu Thr Gly Val Ile Thr
            595                 600                 605

Ser Ser Gly Ser Asn Ile Pro Glu Ile Ile Ser Leu Asp
            610                 615                 620

<210> SEQ ID NO 7
<211> LENGTH: 510
<212> TYPE: PRT
<213> ORGANISM: Human

<400> SEQUENCE: 7

Met Met Ala Glu Leu Val Glu Ala Lys Asn Met Val Met Ser Phe Arg
  1               5                  10                  15

Val Ser Asp Leu Gln Met Leu Leu Gly Phe Val Gly Arg Ser Lys Ser
             20                  25                  30

Gly Leu Lys His Glu Leu Val Thr Arg Ala Leu Gln Leu Val Gln Phe
         35                  40                  45

Asp Cys Ser Pro Glu Leu Phe Lys Lys Ile Lys Glu Leu Tyr Glu Thr
     50                  55                  60

Arg Tyr Ala Lys Lys Asn Ser Glu Pro Ala Pro Gln Pro His Arg Pro
```

```
              65                  70                  75                  80
Leu Asp Pro Leu Thr Met His Ser Thr Tyr Asp Arg Ala Gly Ala Val
                    85                  90                  95
Pro Arg Thr Pro Leu Ala Gly Pro Asn Ile Asp Tyr Pro Val Leu Tyr
                100                 105                 110
Gly Lys Tyr Leu Asn Gly Leu Gly Arg Leu Pro Ala Lys Thr Leu Lys
                115                 120                 125
Pro Glu Val Arg Leu Val Lys Leu Pro Phe Phe Asn Met Leu Asp Glu
                130                 135                 140
Leu Leu Lys Pro Thr Glu Leu Val Pro Gln Asn Asn Glu Lys Leu Gln
145                 150                 155                 160
Glu Ser Pro Cys Ile Phe Ala Leu Thr Pro Arg Gln Val Glu Leu Ile
                165                 170                 175
Arg Lys Phe Gln Gly Met Gln Pro Gly Val Lys Ala Val Gln Val Val
                180                 185                 190
Leu Arg Ile Cys Tyr Ser Asp Thr Ser Cys Pro Gln Glu Asp Gln Tyr
                195                 200                 205
Pro Pro Asn Ile Ala Val Lys Val Asn His Ser Tyr Cys Ser Val Pro
                210                 215                 220
Gly Tyr Tyr Pro Ser Asn Lys Pro Gly Val Glu Pro Lys Arg Pro Cys
225                 230                 235                 240
Arg Pro Ile Asn Leu Thr His Leu Met Tyr Leu Ser Ser Ala Thr Asn
                245                 250                 255
Arg Ile Thr Val Thr Trp Gly Asn Tyr Gly Lys Ser Tyr Ser Val Ala
                260                 265                 270
Leu Tyr Leu Val Arg Gln Leu Thr Ser Ser Glu Leu Leu Gln Arg Leu
                275                 280                 285
Lys Thr Ile Gly Val Lys His Pro Glu Leu Cys Lys Ala Leu Val Lys
                290                 295                 300
Glu Lys Leu Arg Leu Asp Pro Asp Ser Glu Ile Ala Thr Thr Gly Val
305                 310                 315                 320
Arg Val Ser Leu Ile Cys Pro Leu Val Lys Met Arg Leu Ser Val Pro
                325                 330                 335
Cys Arg Ala Glu Thr Cys Ala His Leu Gln Cys Phe Asp Ala Val Phe
                340                 345                 350
Tyr Ile Gln Met Asn Glu Lys Lys Pro Thr Trp Met Cys Pro Val Cys
                355                 360                 365
Asp Lys Pro Ala Pro Tyr Asp Gln Leu Ile Ile Asp Gly Leu Leu Ser
                370                 375                 380
Lys Ile Leu Ser Glu Cys Glu Asp Ala Asp Glu Ile Glu Tyr Leu Val
385                 390                 395                 400
Asp Gly Ser Trp Cys Pro Ile Arg Ala Glu Lys Glu Arg Ser Cys Ser
                405                 410                 415
Pro Gln Gly Ala Ile Leu Val Leu Gly Pro Ser Asp Ala Asn Gly Leu
                420                 425                 430
Leu Pro Ala Pro Ser Val Asn Gly Ser Gly Ala Leu Gly Ser Thr Gly
                435                 440                 445
Gly Gly Gly Pro Val Gly Ser Met Glu Asn Gly Lys Pro Gly Ala Asp
                450                 455                 460
Val Val Asp Leu Thr Leu Asp Ser Ser Ser Ser Glu Asp Glu Glu
465                 470                 475                 480
Glu Glu Glu Glu Glu Glu Asp Glu Asp Glu Glu Gly Pro Arg Pro
                485                 490                 495
```

```
Lys Arg Arg Cys Pro Phe Gln Lys Gly Leu Val Pro Ala Cys
        500                 505                 510
```

<210> SEQ ID NO 8
<211> LENGTH: 1755
<212> TYPE: DNA
<213> ORGANISM: Human

<400> SEQUENCE: 8

| | | | | | |
|---|---|---|---|---|---|
| atggtgatga | gtttccgggt | gtctgagctc | caggtgcttc | ttggctttgc | tggccggaac | 60 |
| aagagtggac | ggaagcacga | gctcctggcc | aaggctctgc | acctcctgaa | gtccagctgt | 120 |
| gcccctagtg | tccagatgaa | gatcaaagag | ctttaccgac | gacgctttcc | ccggaagacc | 180 |
| ctggggccct | ctgatctctc | ccttctctct | ttgcccctg | gcacctctcc | tcctgtgcac | 240 |
| cctgatgtca | ccatgaaacc | attgcccttc | tatgaagtct | atggggagct | catccggccc | 300 |
| accacccttg | catccacttc | tagccagcgg | tttgaggaag | cgcactttac | ctttgccctc | 360 |
| acacccagc | aagtgcagca | gattcttaca | tccagagagg | ttctgccagg | agccaaatgt | 420 |
| gattatacca | tacaggtgca | gctaaggttc | tgtctctgtg | agaccagctg | cccccaggaa | 480 |
| gattattttc | cccccaacct | ctttgtcaag | gtcaatggga | aactgtgccc | cctgccgggt | 540 |
| taccttcccc | caaccaagaa | tggggccgag | ccaagaggcc | cagccgcccc | atcaacatca | 600 |
| caccctggc | tcgactctca | gccactgttc | ccaacaccat | tgtggtcaat | tggtcatctg | 660 |
| agttcggacg | gaattactcc | ttgtctgtgt | accttggtga | ggcagttgac | tgcaggaacc | 720 |
| cttctacaaa | aactcagagc | aaagggtatc | cggaacccag | accactcgcg | ggcactgatc | 780 |
| aaggagaaat | tgactgctga | ccctgacagt | gaggtggcca | ctacaagtct | tccgggtgtc | 840 |
| actcatgtgc | ccgctaggaa | gatgcgcctg | actgtccctt | gtcgtgccct | cacctgcgcc | 900 |
| cacctgcaga | gcttcgatgc | tgcccttat | ctacagatga | atgagaagaa | gcctacatgg | 960 |
| acatgtcctg | tgtgtgacaa | gaaggctccc | tatgaatctc | ttatcattga | tggtttattt | 1020 |
| atggagattc | ttagttcctg | ttcagattgt | gatgagatcc | aattcatgga | agatggatcc | 1080 |
| tggtgcccaa | tgaaacccaa | gaaggaggca | tctgaggttt | gccccccgcc | agggtatggg | 1140 |
| ctggatggcc | tccagtacag | cccaggtcca | gggggagat | ccatcgagaa | taagaagaag | 1200 |
| gtcgaagtta | ttgacttgac | aatagaaagc | tcatcagatg | aggaggatct | gccccctacc | 1260 |
| aagaagcact | gttctgtcac | ctcagctgcc | atcccggccc | tacctggaag | caaaggagtc | 1320 |
| ctgacatctg | gccaccagcc | atcctcggtg | ctaaggagcc | ctgctatggg | cacgttgggt | 1380 |
| ggggatttcc | tgtccagtct | cccactacat | gagtacccac | ctgccttccc | actgggagcc | 1440 |
| gacatccaag | gtttagattt | attttcattt | cttcagacag | agagtcagca | ctatggcccc | 1500 |
| tctgtcatca | tctcactaga | tgaacaggat | gcccttggcc | acttcttcca | gtaccgaggg | 1560 |
| acccccttctc | actttctggg | cccactggcc | ccacgctgg | ggagctccca | ctgcagcgcc | 1620 |
| actccggcgc | ccctcctgg | ccgtgtcagc | agcattgtgg | ccctgggg | ggccttgagg | 1680 |
| gaggggcatg | gaggacccct | gccctcaggt | ccctctttga | ctggctgtcg | gtcagacatc | 1740 |
| atttccctgg | actga | | | | | 1755 |

<210> SEQ ID NO 9
<211> LENGTH: 583
<212> TYPE: PRT
<213> ORGANISM: Human

<400> SEQUENCE: 9

```
Met Val Met Ser Phe Arg Val Ser Glu Leu Gln Val Leu Leu Gly Phe
 1               5                  10                  15

Ala Gly Arg Asn Lys Ser Gly Arg Lys His Glu Leu Leu Ala Lys Ala
            20                  25                  30

Leu His Leu Leu Lys Ser Ser Cys Ala Pro Ser Val Gln Met Lys Ile
            35                  40                  45

Lys Glu Leu Tyr Arg Arg Arg Phe Pro Arg Lys Thr Leu Gly Pro Ser
 50                  55                  60

Asp Leu Ser Leu Leu Ser Leu Pro Pro Gly Thr Ser Pro Val His
 65                  70                  75                  80

Pro Asp Val Thr Met Lys Pro Leu Pro Phe Tyr Glu Val Tyr Gly Glu
                85                  90                  95

Leu Ile Arg Pro Thr Thr Leu Ala Ser Thr Ser Ser Gln Arg Phe Glu
                100                 105                 110

Glu Ala His Phe Thr Phe Ala Leu Thr Pro Gln Gln Leu Gln Gln Ile
                115                 120                 125

Leu Thr Ser Arg Glu Val Leu Pro Gly Ala Lys Cys Asp Tyr Thr Ile
 130                 135                 140

Gln Val Gln Leu Arg Phe Cys Leu Cys Glu Thr Ser Cys Pro Gln Glu
 145                 150                 155                 160

Asp Tyr Phe Pro Pro Asn Leu Phe Val Lys Val Asn Gly Lys Leu Cys
                 165                 170                 175

Pro Leu Pro Gly Tyr Leu Pro Pro Thr Lys Asn Gly Ala Glu Pro Arg
                 180                 185                 190

Gly Pro Ala Val Arg Ser Thr His Pro Trp Leu Asp Ser Gln Pro
                 195                 200                 205

Leu Ser Pro Thr Pro Ser Leu Leu Ile Gly Met Leu Ser Leu Asp Gly
                 210                 215                 220

Ile Thr Pro Cys Pro Cys Leu Val Arg Gln Leu Thr Ala Gly Thr Leu
 225                 230                 235                 240

Leu Gln Lys Leu Arg Ala Lys Gly Ile Arg Asn Pro Asp His Ser Arg
                 245                 250                 255

Ala Leu Ile Lys Glu Lys Leu Thr Ala Asp Pro Asp Ser Glu Val Ala
                 260                 265                 270

Thr Thr Ser Leu Pro Gly Val Thr His Val Pro Ala Arg Lys Met Arg
                 275                 280                 285

Leu Thr Val Pro Cys Arg Ala Leu Thr Cys Ala His Leu Gln Ser Phe
                 290                 295                 300

Asp Ala Ala Leu Tyr Leu Gln Met Asn Glu Lys Lys Pro Thr Trp Thr
 305                 310                 315                 320

Cys Pro Val Cys Asp Lys Lys Ala Pro Tyr Glu Ser Leu Ile Ile Asp
                 325                 330                 335

Gly Leu Phe Met Glu Ile Leu Asn Ser Cys Ser Asp Cys Asp Glu Ile
                 340                 345                 350

Gln Phe Met Glu Asp Gly Ser Trp Cys Pro Met Lys Pro Lys Lys Glu
                 355                 360                 365

Ala Ser Glu Val Cys Pro Pro Gly Tyr Gly Leu Asp Gly Leu Gln
                 370                 375                 380

Tyr Ser Ala Val Gln Glu Gly Ile Gln Pro Glu Ser Lys Lys Arg Val
 385                 390                 395                 400

Glu Val Ile Asp Leu Thr Ile Glu Ser Ser Ser Asp Glu Glu Asp Leu
                 405                 410                 415
```

-continued

```
Pro Pro Thr Lys Lys Gln Cys Ser Val Thr Ser Ala Ala Ile Pro Ala
            420                 425                 430

Leu Leu Gly Ser Lys Gly Val Leu Thr Ser Gly His Gln Pro Ser Ser
            435                 440                 445

Val Leu Arg Ser Pro Ala Met Gly Thr Leu Gly Ser Asp Phe Leu Ser
            450                 455                 460

Ser Leu Pro Val His Glu Tyr Pro Pro Ala Phe Pro Leu Gly Ala Asp
465                 470                 475                 480

Ile Gln Gly Leu Asp Leu Phe Ser Phe Leu Gln Thr Glu Ser Gln Gln
                485                 490                 495

Tyr Gly Pro Ser Val Ile Ile Ser Leu Asp Glu Gln Asp Thr Leu Gly
            500                 505                 510

His Phe Phe Gln Tyr Arg Gly Thr Pro Ser His Phe Leu Gly Pro Leu
            515                 520                 525

Ala Pro Thr Leu Gly Ser Cys His Gly Ser Ser Thr Pro Ala Pro Pro
            530                 535                 540

Pro Gly Arg Val Ser Ser Ile Val Ala Pro Gly Ser Ser Leu Arg Glu
545                 550                 555                 560

Gly His Gly Gly Pro Leu Pro Ser Gly Pro Ser Leu Thr Gly Cys Arg
                565                 570                 575

Ser Asp Val Ile Ser Leu Asp
                580

<210> SEQ ID NO 10
<211> LENGTH: 584
<212> TYPE: PRT
<213> ORGANISM: Mouse

<400> SEQUENCE: 10

Met Val Met Ser Phe Arg Val Ser Glu Leu Gln Val Leu Leu Gly Phe
  1               5                  10                  15

Ala Gly Arg Asn Lys Ser Gly Arg Lys His Glu Leu Leu Ala Lys Ala
                20                  25                  30

Leu His Leu Leu Lys Ser Ser Cys Ala Pro Ser Val Gln Met Lys Ile
            35                  40                  45

Lys Glu Leu Tyr Arg Arg Arg Phe Pro Arg Lys Thr Leu Gly Pro Ser
    50                  55                  60

Asp Leu Ser Leu Leu Ser Leu Pro Pro Gly Thr Ser Pro Pro Val His
65                  70                  75                  80

Pro Asp Val Thr Met Lys Pro Leu Pro Phe Tyr Glu Val Tyr Gly Glu
                85                  90                  95

Leu Ile Arg Pro Thr Thr Leu Ala Ser Thr Ser Ser Gln Arg Phe Glu
            100                 105                 110

Glu Ala His Phe Thr Phe Ala Leu Thr Pro Gln Gln Val Gln Gln Ile
            115                 120                 125

Leu Thr Ser Arg Glu Val Leu Pro Gly Ala Lys Cys Asp Tyr Thr Ile
    130                 135                 140

Gln Val Gln Leu Arg Phe Cys Leu Cys Glu Thr Ser Cys Pro Gln Glu
145                 150                 155                 160

Asp Tyr Phe Pro Pro Asn Leu Phe Val Lys Val Asn Gly Lys Leu Cys
                165                 170                 175

Pro Leu Pro Gly Tyr Leu Pro Pro Thr Lys Asn Gly Ala Glu Pro Arg
            180                 185                 190

Gly Pro Ala Ala Pro Ser Thr Ser His Pro Trp Leu Asp Ser Gln Pro
            195                 200                 205
```

```
Leu Phe Pro Thr Pro Leu Trp Ser Ile Gly His Leu Ser Ser Asp Gly
    210                 215                 220

Ile Thr Pro Cys Leu Cys Thr Leu Val Arg Gln Leu Thr Ala Gly Thr
225                 230                 235                 240

Leu Leu Gln Lys Leu Arg Ala Lys Gly Ile Arg Asn Pro Asp His Ser
                245                 250                 255

Arg Ala Leu Ile Lys Glu Lys Leu Thr Ala Asp Pro Asp Ser Glu Val
            260                 265                 270

Ala Thr Thr Ser Leu Pro Gly Val Thr His Val Pro Ala Arg Lys Met
        275                 280                 285

Arg Leu Thr Val Pro Cys Arg Ala Leu Thr Cys Ala His Leu Gln Ser
    290                 295                 300

Phe Asp Ala Ala Leu Tyr Leu Gln Met Asn Glu Lys Lys Pro Thr Trp
305                 310                 315                 320

Thr Cys Pro Val Cys Asp Lys Lys Ala Pro Tyr Glu Ser Leu Ile Ile
                325                 330                 335

Asp Gly Leu Phe Met Glu Ile Leu Ser Ser Cys Ser Asp Cys Asp Glu
            340                 345                 350

Ile Gln Phe Met Glu Asp Gly Ser Trp Cys Pro Met Lys Pro Lys Lys
        355                 360                 365

Glu Ala Ser Glu Val Cys Pro Pro Gly Tyr Gly Leu Asp Gly Leu
    370                 375                 380

Gln Tyr Ser Pro Gly Pro Gly Gly Arg Ser Ile Glu Asn Lys Lys Lys
385                 390                 395                 400

Val Glu Val Ile Asp Leu Thr Ile Glu Ser Ser Asp Glu Glu Asp
                405                 410                 415

Leu Pro Pro Thr Lys Lys His Cys Ser Val Thr Ser Ala Ala Ile Pro
            420                 425                 430

Ala Leu Pro Gly Ser Lys Gly Val Leu Thr Ser Gly His Gln Pro Ser
        435                 440                 445

Ser Val Leu Arg Ser Pro Ala Met Gly Thr Leu Gly Gly Asp Phe Leu
    450                 455                 460

Ser Ser Leu Pro Leu His Glu Tyr Pro Pro Ala Phe Pro Leu Gly Ala
465                 470                 475                 480

Asp Ile Gln Gly Leu Asp Leu Phe Ser Phe Leu Gln Thr Glu Ser Gln
                485                 490                 495

His Tyr Gly Pro Ser Val Ile Ile Ser Leu Asp Glu Gln Asp Ala Leu
            500                 505                 510

Gly His Phe Phe Gln Tyr Arg Gly Thr Pro Ser His Phe Leu Gly Pro
        515                 520                 525

Leu Ala Pro Thr Leu Gly Ser Ser His Cys Ser Ala Thr Pro Ala Pro
    530                 535                 540

Pro Pro Gly Arg Val Ser Ser Ile Val Ala Pro Gly Gly Ala Leu Arg
545                 550                 555                 560

Glu Gly His Gly Gly Pro Leu Pro Ser Gly Pro Ser Leu Thr Gly Cys
                565                 570                 575

Arg Ser Asp Ile Ile Ser Leu Asp
            580

<210> SEQ ID NO 11
<211> LENGTH: 1955
<212> TYPE: DNA
<213> ORGANISM: Mouse
```

```
<400> SEQUENCE: 11
atggcggaca gtgcggaact aaagcaaatg gttatgagcc ttagagtttc tgaactccaa      60
gtactgttgg gctacgctgg gaggaacaag cacggacgca aacacgaact tcttacaaaa     120
gccctgcatt tgttaaaggc tggctgtagt cctgctgtac aaatgaaaat taagaactc      180
tacaggaggc ggttccctca gaaaattatg acgcctgcgg acttgtctat ccccaacgta     240
cattcaagtc ctatgcctcc gactctttct cgatccacca ttccacagct cacttatgat     300
ggccaccctg catcatcccc actactccct gtttctcttc tgggacccaa acatgaactg     360
gaactcccac atctcacgtc agcgctgcac ccagtccacc cgacataaag ctgcagaagc     420
taccattcta tgacctgttg atgaactga tcaagcccac cagtctagct tcagacaaca     480
gccagcgctt tcgggaaacc tgttttgcat ttgccttgac accacaacag gtgcagcaga     540
tcagcagctc catggatatt ctgggaccaa aatgtgactt cacagtgcag gtccaattaa     600
ggttttgttt atcagaaacc agttgtccac aagaagatca cttccaccc aacctttgtg      660
taaaagtgaa tacaaaacct tgcagccttc caggttacct tccacctact aaaaacggtg     720
tggaaccaaa gcgacctagc cgaccaatta atatcacctc acttgtccga ttgtccacga     780
cagtaccaaa taccattgtt gtttcttgga ctgcagaaat tggaagaacc tattccatgg     840
cagtatatct tgtaaaacag ttgtcctcaa cagttcttct tcagaggtta cgagcaaagg     900
gaataaggaa tccggatcat tctagagctt taattaaaga gaagttaact gcagattcag     960
atagtgagat agctactacc agcctacggg tttcgctgct gtgtccactt gggaaaatgc    1020
gactgacaat ccctgtcgg gcacttacct gctcccacct tcagtgtttt gatgcaactc     1080
tttacattca atgaatgag aaaaaaccaa catgggtttg tcctgtctgt gataagaagg     1140
ccccatatga acaccttatt attgacgggt tgtttatgga aattctaaag tactgcacag    1200
actgtgacga gatacagttt aaggaggatg gctcgtgggc tccaatgagg tcaaagaagg    1260
aggttcaaga agtcactgcc tcctacaatg gagttgatgg ttgcttgagc tccacattgg    1320
agcatcaggt agcgtcccac aaccagtcct caaataaaaa caagaaagtc gaggtcattg    1380
acctaaccat tgacagctcg tcagatgaag aggaggaaga accccctgcc aagaggacct    1440
gtccttccct gtctcctacg tcaccactaa gtaataaagg catttttaagt cttcctcatc    1500
aagcctcgcc tgtgtcccgc acccccaagcc ttcctgctgt agatacaagc tacatcaaca    1560
cctccctcat ccaggactac aggcaccct tccacatgac gcctatgcct tatgacttac     1620
aaggattaga tttctttcct ttcttatcag gagacaatca gcattacaac acctccctgc    1680
tagccgcagc tgcagcggcg gtctcagatg accaggacct cctgcactcc tcccggtttt    1740
tcccgtatac ctcctcgcag atgtttctcg accagctaag tgcaggaggg agcacatctc    1800
tgccagccac caacggaagc agtagcggca gcaacagcag ccttgtgtct tccaacagtc    1860
tgagagagag ccatggccat ggtgtggcca gcaggagcag cgcagacaca gcgtccatct    1920
ttggcatcat accagacatt atctcattgg actga                              1955
```

<210> SEQ ID NO 12
<211> LENGTH: 651
<212> TYPE: PRT
<213> ORGANISM: Mouse

<400> SEQUENCE: 12

Met Ala Asp Ser Ala Glu Leu Lys Gln Met Val Met Ser Leu Arg Val
 1               5                  10                  15

-continued

```
Ser Glu Leu Gln Val Leu Leu Gly Tyr Ala Gly Arg Asn Lys His Gly
         20                  25                  30

Arg Lys His Glu Leu Leu Thr Lys Ala Leu His Leu Leu Lys Ala Gly
         35                  40                  45

Cys Ser Pro Ala Val Gln Met Lys Ile Lys Glu Leu Tyr Arg Arg Arg
 50                      55                  60

Phe Pro Gln Lys Ile Met Thr Pro Ala Asp Leu Ser Ile Pro Asn Val
 65                  70                  75                  80

His Ser Ser Pro Met Pro Pro Thr Leu Ser Pro Ser Thr Ile Pro Gln
                 85                  90                  95

Leu Thr Tyr Asp Gly His Pro Ala Ser Ser Pro Leu Leu Pro Val Ser
             100                 105                 110

Leu Leu Gly Pro Lys His Glu Leu Glu Leu Pro His Leu Thr Ser Ala
         115                 120                 125

Leu His Pro Val His Pro Asp Ile Lys Leu Gln Lys Leu Pro Phe Tyr
     130                 135                 140

Asp Leu Leu Asp Glu Leu Ile Lys Pro Thr Ser Leu Ala Ser Asp Asn
145                 150                 155                 160

Ser Gln Arg Phe Arg Glu Thr Cys Phe Ala Phe Ala Leu Thr Pro Gln
                165                 170                 175

Gln Val Gln Gln Ile Ser Ser Ser Met Asp Ile Ser Gly Thr Lys Cys
            180                 185                 190

Asp Phe Thr Val Gln Val Gln Leu Arg Phe Cys Leu Ser Glu Thr Ser
        195                 200                 205

Cys Pro Gln Glu Asp His Phe Pro Pro Asn Leu Cys Val Lys Val Asn
210                 215                 220

Thr Lys Pro Cys Ser Leu Pro Gly Tyr Leu Pro Pro Thr Lys Asn Gly
225                 230                 235                 240

Val Glu Pro Lys Arg Pro Ser Arg Pro Ile Asn Ile Thr Ser Leu Val
                245                 250                 255

Arg Leu Ser Thr Thr Val Pro Asn Thr Ile Val Val Ser Trp Thr Ala
            260                 265                 270

Glu Ile Gly Arg Thr Tyr Ser Met Ala Val Tyr Leu Val Lys Gln Leu
        275                 280                 285

Ser Ser Thr Val Leu Leu Gln Arg Leu Arg Ala Lys Gly Ile Arg Asn
    290                 295                 300

Pro Asp His Ser Arg Ala Leu Ile Lys Glu Lys Leu Thr Ala Asp Ser
305                 310                 315                 320

Asp Ser Glu Ile Ala Thr Thr Ser Leu Arg Val Ser Leu Leu Cys Pro
                325                 330                 335

Leu Gly Lys Met Arg Leu Thr Ile Pro Cys Arg Ala Leu Thr Cys Ser
            340                 345                 350

His Leu Gln Cys Phe Asp Ala Thr Leu Tyr Ile Gln Met Asn Glu Lys
        355                 360                 365

Lys Pro Thr Trp Val Cys Pro Val Cys Asp Lys Lys Ala Pro Tyr Glu
    370                 375                 380

Met Leu Ile Ile Asp Gly Leu Phe Met Glu Ile Leu Lys Tyr Cys Thr
385                 390                 395                 400

Asp Cys Asp Glu Ile Gln Phe Lys Glu Asp Gly Ser Trp Ala Pro Met
                405                 410                 415

Arg Ser Lys Lys Glu Val Gln Glu Val Thr Ala Ser Tyr Asn Gly Val
            420                 425                 430

Asp Gly Cys Leu Ser Ser Thr Leu Glu His Gln Val Ala Ser His Asn
```

-continued

```
                 435                 440                 445
Gln Ser Ser Asn Lys Asn Lys Val Glu Val Ile Asp Leu Thr Ile
        450                 455                 460
Asp Ser Ser Asp Glu Glu Glu Glu Pro Pro Ala Lys Arg Thr
465                 470                 475                 480
Cys Pro Ser Leu Ser Pro Thr Ser Pro Leu Ser Asn Lys Gly Ile Leu
                485                 490                 495
Ser Leu Pro His Gln Ala Ser Pro Val Ser Arg Thr Pro Ser Leu Pro
            500                 505                 510
Ala Val Asp Thr Ser Tyr Ile Asn Thr Ser Leu Ile Gln Asp Tyr Arg
        515                 520                 525
His Pro Phe His Met Thr Pro Met Pro Tyr Asp Leu Gln Gly Leu Asp
    530                 535                 540
Phe Phe Pro Phe Leu Ser Gly Asp Asn Gln His Tyr Asn Thr Ser Leu
545                 550                 555                 560
Leu Ala Ala Ala Ala Ala Val Ser Asp Asp Gln Asp Leu Leu His
                565                 570                 575
Ser Ser Arg Phe Phe Pro Tyr Thr Ser Ser Gln Met Phe Leu Asp Gln
            580                 585                 590
Leu Ser Ala Gly Gly Ser Thr Ser Leu Pro Ala Thr Asn Gly Ser Ser
        595                 600                 605
Ser Gly Ser Asn Ser Ser Leu Val Ser Ser Asn Ser Leu Arg Glu Ser
    610                 615                 620
His Gly His Gly Val Ala Ser Arg Ser Ser Ala Asp Thr Ala Ser Ile
625                 630                 635                 640
Phe Gly Ile Ile Pro Asp Ile Ile Ser Leu Asp
                645                 650
```

<210> SEQ ID NO 13
<211> LENGTH: 1752
<212> TYPE: DNA
<213> ORGANISM: Mouse

<400> SEQUENCE: 13

```
atggtgatga gtttccgagt gtctgagctc caggtgctcc tcggcttcgc tgcaggaac      60
aagagtgggc ggaaacacga gctgctggcc aaggccctgc acctcctcaa gtctagctgc   120
gccccccagcg tccagatgaa gatcaaagaa ctttatcgca ggcgctttcc ccggaagacc   180
ctggggcctt ctgatctctc cttgctttct ttgccccctg gcacctctcc tcctgtgcac   240
cccgatgtca ccatgaagcc actgcccttc tatgaagtct atggggagct catccgaccc   300
accacccttg cgtccacctc cagccagagg ttcgaggaag cccacttcac cttcgcgctc   360
actcccagc agctgcagca gattctcacg tccagggaag ttctgccagg agccaagtgt   420
gattacacca taaagtgca gctcagattc tgtctctgtg agaccagctg ccctcaggag   480
gactatttcc cccctaacct ctttgttaag gttaatggga actctgcccc cctgccgggt   540
tacctccctc caaccaagaa tggagctgag cccagaggcc cagccgtccg atcaacatca   600
caccctcggc tcgactctca gccactgtcc ccaacaccat cgttattaat tggtcatctg   660
agtttggacg gaattactcc ttgtccgtgt ctggtgaggc aattgactgc agggacccctt   720
ctacaaaaac tcagagccaa ggggatccgg aatccagacc attcccgggc actgatcaag   780
gagaaactga ctgctgaccc cgacagtgaa gtggctacta caagtctccc gggtgtcact   840
catgtgcccg ctaggaagat gcgcctgact gtcccgtgtc gtgccctcac ctgtgcccat   900
```

```
ctgcagagtt tcgatgctgc cctttatcta cagatgaatg agaagaagcc gacatggacc    960
tgtcctgtgt gtgacaagaa ggctccctat gaatcgctga ttattgatgg tttattcatg   1020
gaaattctta attcctgttc ggattgtgat gagatccagt tcatggaaga tggatcctgg   1080
tgtccgatga aacccaagaa ggaggcatca gaggtttgcc ccccgccagg gtatgggctg   1140
gatggtctcc agtacagcgc agtccaggag ggaattcagc cagagagtaa gaagagggtc   1200
gaagtcattg acttgaccat cgaaagctca tcagatgagg aggatttgcc ccccaccaag   1260
aagcagtgct ctgtcacctc agcggccatt ccagcccttt tgggaagcaa aggagtcctg   1320
acatctggtc accagccatc ttcggtgctg cggagccctg caatgggcac attgggcagt   1380
gatttcctgt ctagtctccc ggtacatgag tacccacctg ccttcccact gggggctgac   1440
atccaaggtt tagatttatt ttctttcctt cagactgaga gtcagcagta cggcccttca   1500
gttatcatct cgctagatga acaggacacc ttgggccatt tcttccagta ccgggggacc   1560
ccttcccact tcctgggccc actggccccc acactgggga gctgtcacgg cagttccact   1620
ccagcgcccc ctcctggtcg tgtcagcagc attgtggctc ctgggagctc cttgagggaa   1680
gggcatggag gacccctgcc ttcaggtccc tctttgactg gctgtcggtc agacgtcatt   1740
tccttggact ga                                                        1752
```